United States Patent [19]
Brewer et al.

[11] Patent Number: 5,694,943
[45] Date of Patent: Dec. 9, 1997

[54] METHOD AND APPARATUS FOR AUTOMATIC, ADAPTIVE, ACTIVE FACILITATION TO ASSESS MYOCARDIAL ELECTRICAL INSTABILITY

[75] Inventors: James E. Brewer, St. Paul; Ehssanollah Taghizadeh, Minneapolis, both of Minn.

[73] Assignee: Clontz Corporation, Woodbury, Minn.

[21] Appl. No.: 678,813

[22] Filed: Jul. 12, 1996

Related U.S. Application Data

[63] Continuation of Ser. No. 395,048, Feb. 27, 1995, Pat. No. 5,555,888.

[51] Int. Cl.[6] .................................................. A61B 5/452
[52] U.S. Cl. ............................................................. 128/702
[58] Field of Search .................................. 128/696, 702, 128/705, 704

[56] References Cited

U.S. PATENT DOCUMENTS

| | | | |
|---|---|---|---|
| 5,117,834 | 6/1992 | Kroll et al. | 128/705 |
| 5,487,391 | 1/1996 | Panescu | 128/696 |

*Primary Examiner*—Scott Getzow
*Attorney, Agent, or Firm*—Skinner and Associates; Joel D. Skinner, Jr.

[57] ABSTRACT

A method and apparatus continuously, automatically, and adaptively facilitate the electrical activity of a patient's heart by pulsing the heart with current. The method and apparatus further continuously, automatically, and adaptively monitor the resulting electrical activity of the patient's heart to assess the patient's likelihood for myocardial electrical instability. The method comprises the steps of injecting current across the patient's heart, monitoring the patient's electrocardiogram for the effects of these current pulses, and adapting the current pulses continuously and automatically to maximize the effects, thereby assessing a patient's likelihood of sudden cardiac death.

30 Claims, 23 Drawing Sheets

METHOD AND APPARATUS FOR AUTOMATIC, ADAPTIVE, ACTIVE FACILITATION TO ASSESS MYOCARDIAL ELECTRICAL INSTABILITY

The present invention is a continuation of U.S. patent application Ser. No. 08/395,048, filed Feb. 27, 1995 now U.S. Pat. No. 5,555,888.

FIELD OF THE INVENTION

This invention relates generally to the analysis of the electrical activity of a patient's heart, and more particularly to the generation and analysis of far-field mediated transmissions of impulses across inexcitable tissues, known as Wedensky facilitation or inhibition, to assess a patient's likelihood for myocardial electrical instability. Further, this invention relates to active electrocardiographic systems and methods, and particularly to an automatic, adapting, active electrocardiography method and apparatus for assessing the electrical instability of the heart by generating and analyzing occurrences of facilitation or inhibition during normal cardiac electrophysiological function.

BACKGROUND OF THE INVENTION

Sudden cardiac death (SCD) has been referred to as the most challenging problem facing contemporary cardiology. Most sudden deaths are unexpected, unheralded by symptoms of any duration or by overt coronary artery disease (CAD). It is thought that the mechanism responsible for the great majority of SCD is ventricular fibrillation (VF), a state in which the normally organized electrical activity of the heart becomes disorganized. This disorganized electrical activity initiates similarly disorganized and ineffectual mechanical contractions of the pumping chambers of the heart, resulting in circulatory collapse and death.

By far the most desirable and potentially the most effective response to the problem of SCD is prevention, in which the first step would be the identification of those individuals at increased risk. It is this identification with which the present invention is concerned.

Once identified, there are several methods to treat such patients. A first method is antiarrhythmic drugs. A second method is implantable defibrillators. A third method is cardiac ablation. Because of the side effects of drugs and the surgical risks involved with the implantable defibrillator and ablation treatments, a patient is examined carefully before receiving a therapy. The patient's propensity for VF is determined by attempting to induce such irregular cardiac behavior through invasive electrophysiological studies. These studies provide the basis for deciding the best treatment for a patient, but the studies themselves involve a significant likelihood of pain and risk of death. There is a need for a noninvasive and safe means of determining which patients are at increased risk for SCD.

The standard method for a noninvasive and safe means to determine a patient's risk of SCD is the time-domain signal averaged electrocardiography (ECG) method and apparatus with the ECG electrodes positioned in the Frank orthogonal configuration. The time-domain signal averaged ECG or its frequency-domain embodiments have been in use for 15 years, and much work has been done to understand its capabilities and limitations. Unfortunately, there are many questions that remain unanswered about the ability of the signal averaged ECG to accurately assess a patient for increased risk of SCD. As recently as June 1994, Hnatkova and colleagues found that different filters and filter settings produce discordant results of the signal averaged ECG when using the same instrument, complicating the well-known fact that the use of different recording systems produces conflicting results (PACE 1994; 17: 1107–1117). Hence, this particular set of prior art methods and devices has been unable to adequately identify patients with an increased risk of SCD. Attempts to use signal averaged ECG therefore have met with limited success.

U.S. Pat. No. 4,802,491 to Cohen and Smith discloses a passive method of detecting subtle alternations in the morphologic features of the ECG, called alternans, to determine a patient's increased risk of SCD. In a study published in the *New England Journal of Medicine* (1994; 330: 235–241) on a small set of patients, Cohen et al. discovered that their method provided a capability equal to that of the signal averaged ECG; in particular, T-wave alternans ratios were greater in patients with inducible arrhythmias when compare to those patients that could not be induced. Unfortunately, their method required the transvenous insertion of a recording-stimulating catheter into a patient's heart, and their apparatus then paced the patient's heart at 100 beats per minute. As discussed in their publication, their method and apparatus were limited by the invasive procedure, and improvements in their method were needed to compensate for fluctuations in heart rate associated with normal sinus rhythm. Additionally, they acknowledged that there are limitations regarding the sensitivity and reliability of their technique. These limitations are derived from the need to distinguish alternans-type fluctuations in the ECG from larger fluctuations due to noise or other physiologic fluctuations such as respiration. Additionally, the Cohen et al. method and apparatus provide a correlational relation between T-wave alternans and the results of electrophysiological testing. No information is provided regarding the actual, anatomical and dynamical state of the heart. Therefore, this prior art device has been unable to provide a noninvasive, safe, and highly accurate means to identify patients with an increased risk of SCD.

To this point then it had not been possible to accurately identify patients with increased risk of SCD in a safe and noninvasive manner. Despite the need for such a method and apparatus, there is only one apparatus, insofar as is known, that is capable of identifying patients with increased risk of SCD safely and noninvasively. The apparatus disclosed in U.S. Pat. Nos. 5,117,834 and 5,351,687 to Kroll et al. (hereinafter called the "Kroll patents") determines the risk of SCD by "microinduction." There are significant limitations to this apparatus.

The Kroll patents disclose that an active, far-field application of current across the heart will change the way diseased cells depolarize, that these changes are seen by surface ECG, and that the method and apparatus can discern these activation changes by computing a specially designed sum of differences between a plurality of current-injected cardiac cycles and undisturbed cardiac cycles. Although the electrocardiographic changes created and measured by the disclosed apparatus are valid, how and why compromised or depressed myocardial substrates provide an electrophysiological dynamic to support the changes incurred by this active facilitation (AF) is subject to criticism.

With a careful review of the published theoretical and clinical research, we ascertain a more complete and appropriate understanding regarding the electrophysiological process of AF that permits us to determine and develop significant improvements over the teachings of the prior art.

We begin by considering the myocardial tissue of the heart. An electrical wave front is propagated across the tissue by the local circuit activity from one cardiac cell to the next through interconnective tissue. The local circuit current in the heart is produced by an intracellular potential gradient and is responsible for the propagation of electrical impulses in excitable tissue. For each cell, the current diffuses electrotonically across the intracellular substrate, is forced outward across the cell membrane by a resulting transmembrane potential, and flows back towards the source through the extracellular space. Due to the resistive nature of the tissue, the resulting membrane depolarization is largest near the source, where the cell is connected to other depolarizing cells, and decreases monotonically with distance. The area of excitable cellular membrane closest to the source is depolarized and generates inward ionic current. Propagation across the cell is attained when the amount of inward current exceeds that amount of the outward current found over the remainder of the membrane. In addition, because overall conduction depends on these local current circuits, the speed at which an electrical wave front is propagated across myocardial tissue is determined by the coupling resistance between cells, such that the propagation velocity decreases with increasing coupling resistance.

Possible causes for propagation failure across a section of tissue can be due to reduced intracellular potential, lowered excitability, or regions of increased tissue resistivity. For example, progressive interstitial fibrosis during aging in myocardial tissues results in a loss of electrical coupling. As another example, disruption of side-to-side connections in ischemic or infarcted tissues increase path lengths and the number of intercellular junctions traversed by an electrical wave front moving in transverse directions. Further, the loss of orientation of the tissue increases the complexity of the tissue and increases activation delay. All of these problems can and do occur in tissue that has been compromised by various heart diseases, such as CAD and its complications of myocardial infarction, acute and chronic ischemia, and congestive heart failure. These problems are well understood, and are described in the published literature, both at a cellular level and at a tissue level. One of the earliest references was by Boineau and Cox in *Circulation* (1973; 48: 702–713), in which they described the desynchronization and marked slowing of previously uniform activation that occurs across infarcted and ischemic tissue. The observed electrical activity resembled abbreviated, local fibrillation. These effects are now called "fractionation." One of the most recent studies was published by de Bakker et al. in *Circulation* (1993; 88: 915–926), demonstrating a "zigzag" course of activation at high speeds. The activation wave front proceeds along circuitous routes lengthened by branching and merging bundles of myocardial tissues that have survived infarction or ischemia.

Regarding these general issues of how electrical wave fronts are conducted across compromised myocardial tissues, Antzelevitch and Moe, in *Circulation Research* (1981; 49: 1129–1139) and the *American Journal of Physiology* (1983; 245: H42–H53), have recently clarified the underlying process of certain types of transmissions by showing that very slow conduction through ischemic areas can result from step delays imposed by electrotonic transmission of impulses across inexcitable or compromised segments of cardiac tissue rather than from uniform slow conduction of propagated action potentials. These subthreshold, electrotonic effects are called Wedensky facilitation or inhibition. In their experiments, they compared the characteristics of impulse conduction across an ischemic gap between two pieces of viable tissue. They showed that transmission across the gap was mediated by electrotonic displacement of membrane potential by subthreshold current pulses of appropriate duration passed through the ischemic gap. The activity recorded from the center of the gap segment was shown to comprise two components when impulse transmission across the ischemic gap was successful. The two components proved to be electrotonic images of the cellular responses at each end of the gap, thereby ruling out the possibility of active participation of the slow inward currents described earlier. Their experimental results suggested that electrotonic delay rather than slow response was responsible for slow conduction observed in depressed or compromised tissue. Antzelevitch et al. also showed that the subthreshold potentials recorded intracellularly from inexcitable zones, referred to as electrotonic potentials, were in fact local depolarizations (or hyperpolarizations), which depended on several variables, including the amount of the inexcitable tissue, tissue resistances, the amplitude of the wave front entering the tissue, and the excitability of the tissue beyond the problem area.

More importantly, their results further showed that the amplitude of an electrotonic potential emerging from the far end of inexcitable tissue must be large enough to bring excitable tissue to threshold if transmission was to succeed, and that the amplitude of the electrotonic potentials varied across the inexcitable tissue with respect to the levels of voltage that were encountered. In an important series of their experiments, they studied the effects of subthreshold depolarizing and hyperpolarizing current pulses on the amplitude of the electrotonic potential. They concluded that subthreshold pulses altered the threshold requirements for subsequent activation at the far end of the inexcitable gap by these traversing electrotonic potentials. They also determined that significant voltage and time dependencies of a facilitating or inhibitory nature existed, such that voltage-dependent effects varied with respect to the timing of delivered pulses.

The results of Antzelevitch et al. therefore provide substantial verification to several conclusions regarding the operational aspects of the present invention. First, Antzelevitch et al. provide significant results regarding the electrophysiological process and the possible effects of an external current pulse placed through the heart. They demonstrated that it is electrotonic delay rather than slow response that is responsible for slow conduction across depressed or inexcitable portions of the myocardium. Therefore, a process of external AF does not cause cells near threshold to necessarily depolarize or hyperpolarize but, rather, the AF enhances (by facilitating) or represses (by inhibiting) the naturally occurring electrotonic propagation of an electrical wave front across a section of compromised myocardial tissue. Therefore, we understand that a external current pulse delivered through the heart will indeed facilitate or inhibit electrical activity across such myocardial tissues, that the facilitation or inhibition from these pulses will indeed incur changes in a cardiac cycle, and that these changes can thereby be discovered with a careful and appropriate analysis of high-fidelity, high-resolution ECG signals taken from a patient's body.

Regarding how and why an external current pulse provides an electrical dynamic to support the changes incurred by active facilitation, far-field facilitation, as embodied by an external current pulse, must occur close to specific times during the cardiac cycle in which the diseased portion of the heart must function. These specific times are directly related to the compromised tissue's ability to allow the effective transfer of current across the tissue itself. Far-field facilitation has diminishing effects the further away in time that it occurs with respect to the conductive performance of the diseased portion of the heart. These specific points are supported by the results of Antzelevitch et al. suggesting that an external current pulse, delivered at the right moment in time, serves to change the membrane potential to allow less constrained, subthreshold depolarization across ischemic or infarcted tissues. The timing of a pulse is therefore critical, as further supported by the frequency-dependent, rate results. Further, delay across depressed tissue depends on the amount of this tissue, so that the size of the depressed tissue may be estimated by a subtle evaluation of the beat-to-beat changes produced by active facilitation.

The Kroll patents clearly show a manually operated, "hit or miss" aspect to a diagnostic strategy, with no effective means to determine how the more subtle aspects of AF can be used to further guide and refine the process of discovering diagnostic levels of myocardial electrical instability. The preferred embodiment of the apparatus shown therein teaches testing of a patient with a large combination of delivered facilitating pulses, in a manner designed to exhaustively search through a list of pulsing parameters and their ranges (such as delivery or sensing electrodes, current levels, pulse durations, and polarity). This diagnostic strategy is a significantly inefficient and possibly ineffective search for changes due to AF. The preferred embodiment of the apparatus further places an undue burden upon the physician to manually discern these subtle effects and to manually combine a large amount of data generated by such an exhaustively long sequence of facilitating pulses in order to guide the diagnostic activity. It is therefore not clear whether the physician can effectively manipulate the delivery of current pulses to implement a successful diagnostic searching strategy. For example, it can be seen to be, at the very least, a time consuming process to pinpoint the best time to deliver a facilitating pulse during a cardiac cycle. The physician is therefore left with relatively coarse results determined by a brute-force process of applying these pulses.

In a short paragraph referred to as an alternative embodiment, the Kroll patents propose a capability of varying the location of facilitating pulses until a maximal response is found, and then fixing the facilitating pulse to this timing location. It is clear from the teachings and implementation of the Kroll patents, however, that the positioning of the facilitating pulse to such a maximally responsive location is a manual and haphazard process by design, and does not in any way anticipate the present invention and its preferred embodiment as a significantly effective means to automate the diagnostic process of determining a level of myocardial electrical instability and thereby diagnosing a patient's risk for SCD.

The invention provides a method and apparatus to automatically and adaptively search for and discover the level of electrical instability of the heart by pulsing across a plurality of cardiac cycles in a way to optimally capture the electrophysiological information that indicates the possible location and amount of each diseased part. To this end, we describe a method and apparatus that are capable of diagnosing patients for increased levels of risk of SCD by using AF, externally and electrically probing the heart to provide an anatomical and electrophysiological assessment of a patient's damaged myocardium. We specifically propose to automate the process of AF (as defined by monitoring and evaluating outcomes from applying a sequence of current pulses to the heart) by defining and controlling a next AF step of this process according to the type of electrical response elicited from the myocardium due to a prior AF step. To realize this conceptual picture, we propose to use a nonlinear optimization method, called the simplex method, to iteratively evaluate a special "objective function" with inputs taken from a special "parameter-outcome" space. The simplex method and its searching strategy is therefore used to determine the next sequence of current pulses and their corresponding delivery across the heart according to the electrical activity measured from the delivery of a prior sequence of pulses.

The simplex method tracks optimum operating conditions for a process by evaluating an outcome from the process at a set of parameter points, or vertices, which form a simplex on a hypersurface defined in a parameter-outcome space, and continually forms new simplices by reflecting one point of a simplex in a hyperplane of the remaining points of the simplex. The simplex method adapts the simplex to the local landscape of the parameter-outcome space, elongating down long, inclined planes, changing direction on encountering curves on the surfaces in the space, and contracting in the neighborhood of the objective function's maximum (or minimum, depending on the purpose of the function). The simplex method operates to determine a global maximum value of the objective function as quickly as possible.

In the preferred embodiment of the invention, we construct a parameter-outcome space in which each parameter point or vertex, called an AF parameter point, defines a unique application of active facilitation to a patient's heart, specified by a set of numbers that describes a sequence of current pulses together with a set of corresponding pulse delivery and ECG monitoring instructions. Each parameter point therefore represents a set of instructions explaining how and when to deliver different types of pulses across a plurality of cardiac cycles and how and when to monitor and collect a plurality of ECG signals during this span of cardiac cycles. We use an objective function to facilitate electrical instability as the means to find and compare the subtle differences that may exist among the ECG signals collected during the active facilitation defined by a parameter point.

When an AF parameter point is input to the objective function, the objection function operates the present apparatus to implement AF defined by the parameter point, and computes a value, called the outcome, that represents the amount of difference as measured from the corresponding ECG signals collected during the AF. The simplex method, by the very definition of its searching strategy, actively and automatically selects new AF parameter points to input to the objective function. As described above, these AF parameter points are vertices in a simplex that is continually adapted to a surface in the parameter outcome space, which, indeed, is a surface defined by the outcomes of the objective function. The simplex method searches for and discovers the largest outcome possible by evaluating a continual series of these "AF parameter vertices" with the objective function, using its searching strategy to guarantee that it will find the largest outcome and that it will find this largest outcome in an efficient and effective manner. We define an outcome of the objective function to represent a measure of the electrical instability of a patient's myocardium as elicited by AF. Utilizing the simplex method, the larger an outcome the more likely a patient has a high degree of myocardial electrical instability and thereby the more likely a patient may suffer from SCD.

We use the simplex method as the central element of a control program that automatically evaluates a patient safely and noninvasively to assess a patient's level of myocardial electrical instability. The simplex method, as the central element of the invention's control program, chooses a new sequence of facilitating pulses by predicting the effects that this facilitating sequence will have on the patient's heart. As will become apparent from the description of the invention in the preferred embodiment, the simplex method and the control program that operates this method most specifically overcome the significant limitations of the prior art.

The most effective and efficient way to implement the simplex method is to create an arbitrary, though constrained, sequence of facilitating pulses to "search" the electrical activity in a patient's myocardium. The invention therefore delivers an arbitrary sequence of pulses across the myocardium. Specifically, the invention delivers a plurality of pulses during a cardiac cycle. The invention further delivers any type or shape of current pulse during a cardiac cycle. The invention further acquires a plurality of high-fidelity ECG signals throughout a cardiac cycle whenever the ECG hardware is not blanked during the delivery period of a pulse.

Kavanagh et al. (*PACE* 1990; 13: 1268–1276) augment the clinical work of Antzelevitch et al. by demonstrating that certain types of fields, in the form of pulses, are more effective at incurring threshold or subthreshold action potentials than other types. For example, they showed that it was harder to stimulate a myocardial cell when its action potential at rest was higher than it would be under normal conditions. Normal myocardial cells have a resting transmembrane potential of approximately –90 mV. In the single cell model of the experiment, the application of a short depolarizing stimulation alone failed to evoke a response from a group of cells held at a resting transmembrane potential of –55 mV. In contrast, while first holding the resting transmembrane potential at –60 mV and then applying a hyperpolarizing pulse to transiently clamp the cells toward a more negative resting potential of –75 to –85 mV, the same depolarizing pulse was able to evoke an action potential, and was able to do so with a substantially shorter pulse. In addition, the hyperpolarizing pulse increased the upstroke velocity and amplitude of the evoked action potential as compared to those occurring with a depolarizing pulse alone. FIGS. 6 and 7 of the Kavanagh publication is particularly instructive regarding the effects of a depolarizing or hyperpolarizing pulse on cells with different values of resting transmembrane potential. The invention delivers a facilitating pulse from any pair of electrodes and with either polarity (positive or negative). The invention further combines two or more pulses to provide a single, shaped, polyphasic pulse.

Recent experiments have studied the effects of external, subthreshold fields, as short pulses, on the excitability of a cardiac cell. The experimental results describing the electrical excitability of a cardiac cell during exposure to an external field demonstrate that a cardiac cell anticipates the arrival of a far-field current pulse such that a pulse can reduce a cell's threshold for stimulation as much as 5 milliseconds before the pulse arrives, and the far-field effects due to a pulse across the cell membrane dissipate quickly after a generating source is removed and a pulse is no longer applied. The invention delivers a pulse at any specific time during a cardiac cycle. The invention delivers a pulse as short as 5 µs in length and requiring a blanking period less than 50 µs.

As a supporting counterpart to the clinical research work described above, many membrane models and computer simulations of action potential stimulation and action potential propagation in ventricular myocardium, based on clinical research data, have been proposed over the last fifty years. Specific to our purposes regarding AF and the invention, two recently published papers contain a significant set of results that further guide the implementation and operation of the invention. In the first paper, Leon and Roberge (*IEEE Transactions on Biomedical Engineering* 1993; 40: 1307–1319) model extracellular stimulation of cardiac cells. Leon and Roberge demonstrated that an effective stimulation of myocytes must take into account the shape of the pulse stimulus and its application in the cardiac cycle. They demonstrated that, because the intracellular space of a cell is very small, the cell's potential is nearly uniform over the length of the cell and the transmembrane potential is governed by the applied field. They further demonstrated that a cathodal (or negative) pulse is a preferred stimulus at diastole, that an anodal (or positive) pulse is a preferred stimulus during the plateau phase of the action potential, and that a biphasic pulse is best during the relative refractory period. The invention delivers biphasic (specifically polyphasic) facilitating pulses.

In a second paper, Pollard, Burgess and Spitzer (*Circulation Research* 1993; 72: 744–756) provided theoretical work with respect to the electrical activity of the heart as a whole. They used computer models which feature histological aspects of the heart to answer questions about how the shaping of the heart muscle can affect the timing and pattern of activation. They showed that portions of activation wave fronts that are aligned with myocardial fibers conduct faster than those wave fronts aligned across fibers, so that fiber rotation of a cardiac cell and inhomogeneous conductivity causes acceleration and deceleration of the spread of the activation wave front across the heart, thereby matching results observed and reported in epicardial activation maps from experimental animal studies. They therefore showed that electrical activity and wave front propagation in myocardium is nonuniformly anisotropic. AF may therefore provide an improved diagnostic ability if it were implemented in an optimal direction through the patient's torso and heart with respect to fiber rotation and orientation of the depressed or compromised tissue. The invention constructs, delivers, and evaluates an arbitrary sequence of facilitating pulses from a plurality of electrode pairs. The invention further provides an optimal means to evaluate the effects of any shaped pulse that is delivered at any time during a cardiac cycle across any specific section of the heart.

Another limitation of the prior art is the lack of teachings regarding the well-known problems that are created by applying electrical current into the body while simultaneously making voltage measurements on the body surface. The process of measuring voltages on a patient's torso must be shielded from the current pulses by breaking the voltage measuring connections for a short period of time. This process of temporarily breaking the measuring connections is called blanking. The invention carefully breaks these measuring connections a short time before a current pulse is delivered to the body, and reconnects them to the body a short time after the delivery. The period of time that the voltage measuring capability is disconnected has been designed to be as short as possible without allowing deleterious effects from a current pulse to affect the measuring process. The apparatus is therefore further able to deliver a current pulse to a patient's body with a minimal loss of monitored voltage information.

Another limitation of the prior art is the lack of teachings regarding the well-known problems that are created by the resistance across the chest when electrical current is placed into the body, and especially across the heart. We have therefore developed and designed hardware capable of overcoming these problems that exist when applying low levels of current through the chest to effect discernible changes in the electrical activity of the heart. Specifically, we have applied a modified version of a prior-art precision current regulator, as described in the preferred embodiment, to overcome these limitations.

SUMMARY OF THE INVENTION

The present invention provides a method and apparatus to automatically generate and analyze far-field mediated transmissions of impulses across inexcitable tissues to assess a patient's likelihood for myocardial electrical instability. A primary object of the invention to provide an automatic, real time ECG method and apparatus for assessing the electrical instability of the heart by generating and analyzing occurrences of facilitation or inhibition during normal cardiac electrophysiological function.

The invention injects a sequence of electromagnetic energy pulses into a patient's body by precisely regulating a programmable, digitally controlled, current source. A bank of high-fidelity, electrocardiographic signal leads and associated data acquisition hardware monitor the patient's electrocardiographic signals. The current injecting hardware and electrocardiographic hardware are controlled by a software program and are microcontrolled by several high performance, programmable, microcontroller integrated circuits that are coupled in a master-slave arrangement and controlled by a master data clock. With this arrangement, the current injecting hardware and the high-fidelity, electrocardiographic hardware are controlled to operate synchronously and in parallel. The electrocardiographic signal hardware utilizes an analog, digitally programmable, active filter that is continuously adapted real-time by the microcontrolling elements to acquire the patient's electrocardiographic signals within several different, predetermined frequency bands.

The invention records the electrophysiological changes in the acquired electrocardiographic signals that are caused by injecting the sequence of electromagnetic energy pulses into a patient's heart. The recorded changes in the electrocardiographic signals are collected into two waveforms called the electrical instability waveform and the facilitated instability waveform.

To construct the electrical instability waveform, the invention extracts and time-wise aligns a group of cardiac cycles from the patient's electrocardiographic signals, computes a square of an algebraic difference between temporally-adjacent pairs of the cardiac cycles, and averages the resulting squared algebraic differences. To construct the facilitated instability waveform, the invention computes a baseline for the electrical instability waveform and subtracts the baseline from the electrical instability waveform.

The facilitated instability waveform is integrated to create a facilitated instability index. The facilitated instability index is formed by summing the facilitated instability waveform, computing a peak to peak amplitude assessment of the electrocardiographic signals, and normalizing the sum by the amplitude assessment.

The invention continuously and automatically adapts the process of injecting electromagnetic energy pulses and monitoring electrocardiographic signals to maximize the recorded changes, particularly the facilitated instability index, by using a nonlinear optimization process called the simplex method, thereby providing a measure of a patient's likelihood of sudden cardiac death.

A further object of the invention is to continuously inject a very high-frequency, high-impedance current source through the system's leads and electrodes, continuously monitoring the voltage levels that are derived from injecting the impedance current source, and signaling an alarm when these voltage levels exceed a predetermined threshold, thereby detecting a electrocardiograph wire or electrode failure.

A further object of the invention is to monitor a patient's electrocardiographic signals prior to injecting electromagnetic energy, thereby recording the natural changes that occur from one cardiac cycle to the next. Following this initial step, the invention injects electromagnetic energy, monitors the patient's electrocardiographic signals, records the facilitated changes, and removes the recorded natural changes from the recorded facilitated changes. The invention thereby removes the confounding effects of naturally occurring physiological variations from an assessment of the patient's likelihood of sudden cardiac death.

The benefits of this invention will become clear and will be best appreciated with reference to the detailed description of the preferred embodiments. Other objects, advantages and novel features will be apparent from the description when read in conjunction with the appended claims and attached drawings.

DESCRIPTION OF THE PREFERRED EMBODIMENTS

Clinical Background and Theory of Operation

The operation of the heart is regulated by electrical signals produced by the heart's sino-atrial (SA) node. Each signal produced by the SA node spreads across the atria and ventricles of the heart, depolarizing the muscle fibers as it spreads. Atrial and ventricular contractions occur as the signal passes. After contracting, the myocardial cells repolarize during a short period of time, returning to their resting state. Once repolarized, the muscle cells are ready to be depolarized again by a signal from the SA node.

At rest, the normal adult SA node produces a signal approximately 60 to 85 times a minute, causing the heart muscle to contract, and thereby pumping blood to the remainder of the body. This constitutes the repetitive, cyclical behavior of the heart. Each cycle in the operation of the heart is called a cardiac cycle.

To analyze the heart's operation, a variety of techniques have been developed for collecting and interpreting data concerning the electrical activity of the heart. One of the most basic of these approaches is the electrocardiograph (ECG). As an electrical signal spreads across the heart, which we shall call an electrical wave front, an ECG repetitively measures the voltages, or "leads," at various electrodes relative to a designated "ground" electrode. The ECG typically plots each lead over an interval of time such that the heart's electrical activity for one or more cardiac cycles is displayed for purposes of monitoring or analysis. The three most common ECGs are known as the "12-lead," the "18-lead," and the vector cardiograph.

A cardiac cycle as measured by the ECG is partitioned into three main elements which reflect the electrical and mechanical operation of the heart. The portion of a cardiac cycle representing atrial depolarization is referred to as a "P-wave." Depolarization of the ventricular muscle fibers is represented by "Q," "R," and "S" points of a cardiac cycle. Collectively these "QRS" points are called an "R-wave" or a "QRS complex." The portion of a cardiac cycle representing repolarization of the ventricular muscle fibers is known as a "T-wave."

Figure 1:
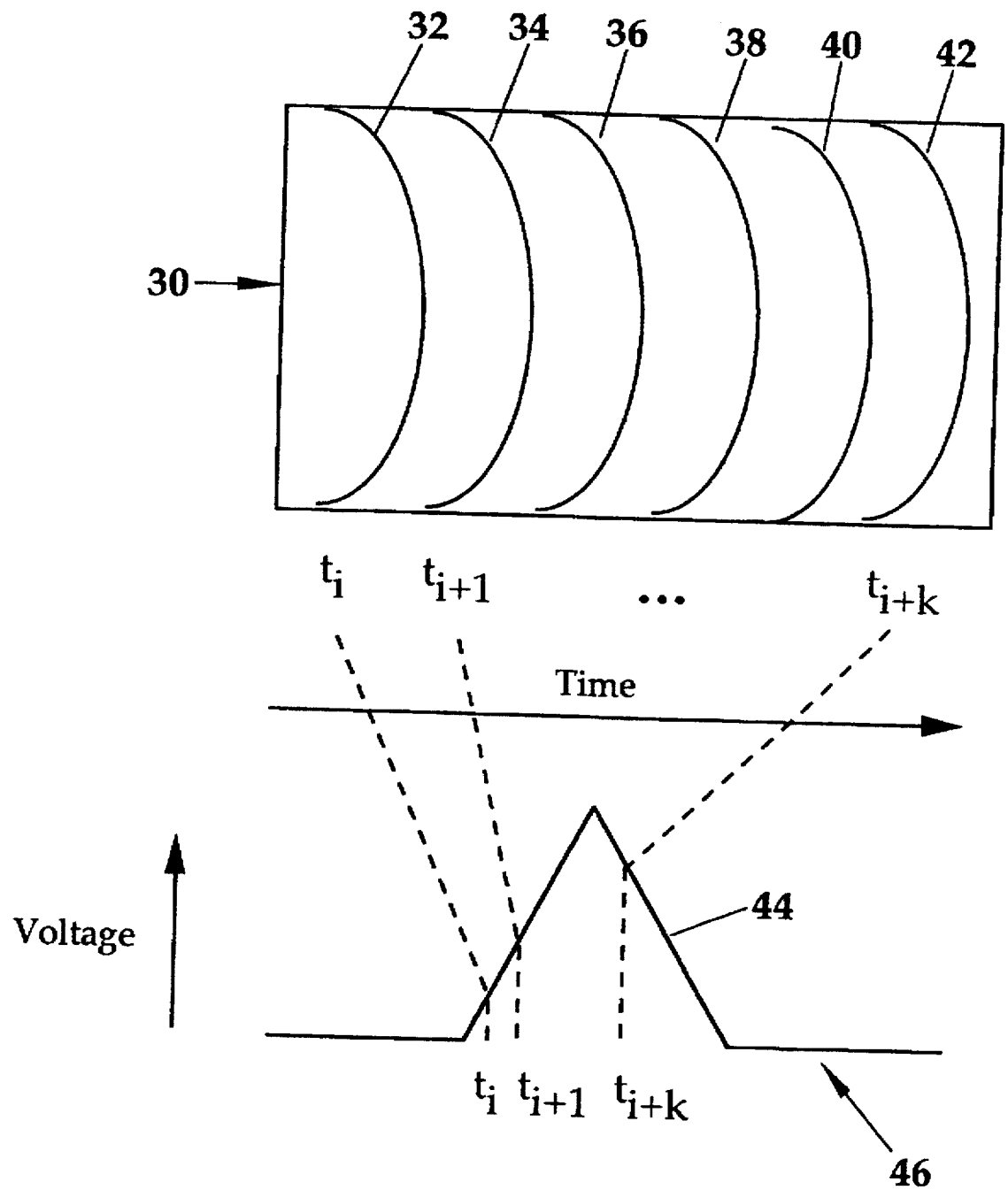
FIG. 1 illustrate a portion of an electrical wave front traveling across normally perfused myocardial tissue, and the corresponding contribution of this portion of the wave front to a R-wave of a cardiac cycle.

FIGS. 1 through 4 illustrate the underlying electrophysiological rationale and operation of the apparatus. FIG. 1 demonstrates the time course of an electrical wave front across a section of myocardial tissue 30. FIG. 1 represents the activity of the wave front across normally perfused tissue 30, where each curved line 32, 34, 36, 38, 40, and 42 across the block of tissue 30 represents the position of the wave front at a point in time during an R-wave 44 of a cardiac cycle 46. The left-most line 32 represents the wave front immediately following the time it first encountered the tissue, at time $t_i$, and the right-most curved line 42 represents the wave front immediately prior to the time it leaves the tissue, at time $t_{i+k}$. The wave front progresses across tissue 30 from $t_i$ to $t_{i+k}$ at a speed regulated by the state of tissue 30 itself. As shown in FIG. 1, wave front 32 remains intact as it moves across the tissue 30. The electrical wave front depicted at 32, 34, 36, 38, 40, and 42 through tissue 30 impacts the R-wave morphology 44 and the measurements thereof, as depicted in FIG. 1 below tissue 30.

Figure 2:
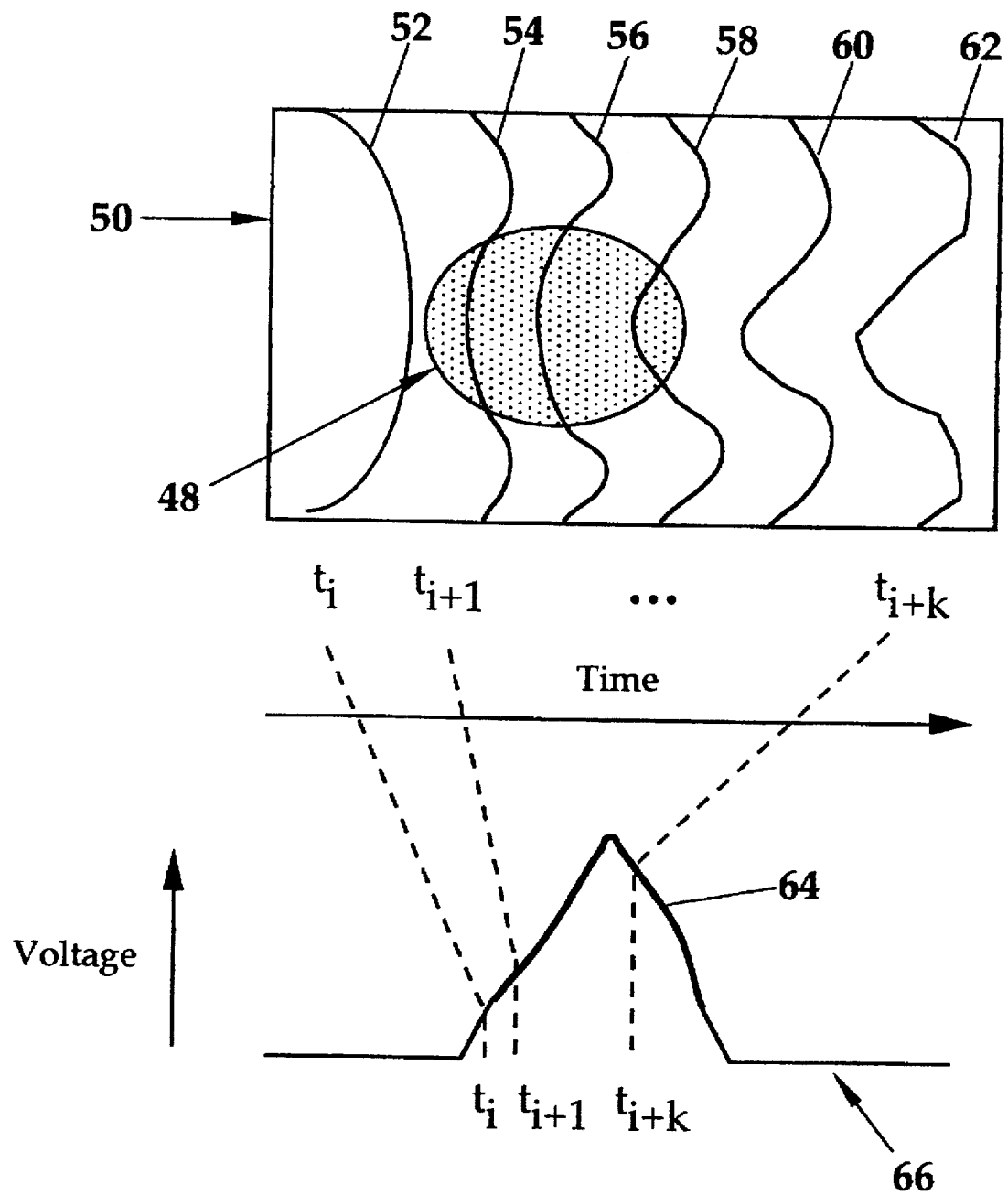
FIG. 2 illustrates a portion of an electrical wave front traveling across compromised or depressed myocardial tissue, and the corresponding contribution of this portion of the wave front to a R-wave of a cardiac cycle.

Similarly, FIG. 2 illustrates a portion of the myocardial tissue 50 that contains a small section 48 that is electrophysiologically compromised or depressed compared to tissue 50 surrounding it. This section 48 of tissue is shown as a small, circular area. This section 48 of tissue represents an ischemic or fibrotic region of the heart due to CAD or a healed myocardial infarction. The wave front depicted at 52, 54, 56, 58, 60, and 62 slows as it travels across depressed section 48. The depressed tissue 48 disrupts the wave front depicted at 52, 54, 56, 58, 60, and 62 from its normal electrical pathways. Indeed, due to the refractory nature of excitable tissues and particularly that of depressed tissues, the time course and pathways of an electrical wave front across a compromised section of tissue changes with each cardiac cycle. As shown in FIG. 2, the wave front depicted at 52, 54, 56, 58, 60, and 62 is "fractured" as it moves across the tissue 50. As before, the electrical wave front depicted at 52, 54, 56, 58, 60, and 62 through tissue 50 impacts the R-wave morphology 64 and 66 and the measurements thereof, as depicted below tissue 50 in FIG. 2.

Figure 3:
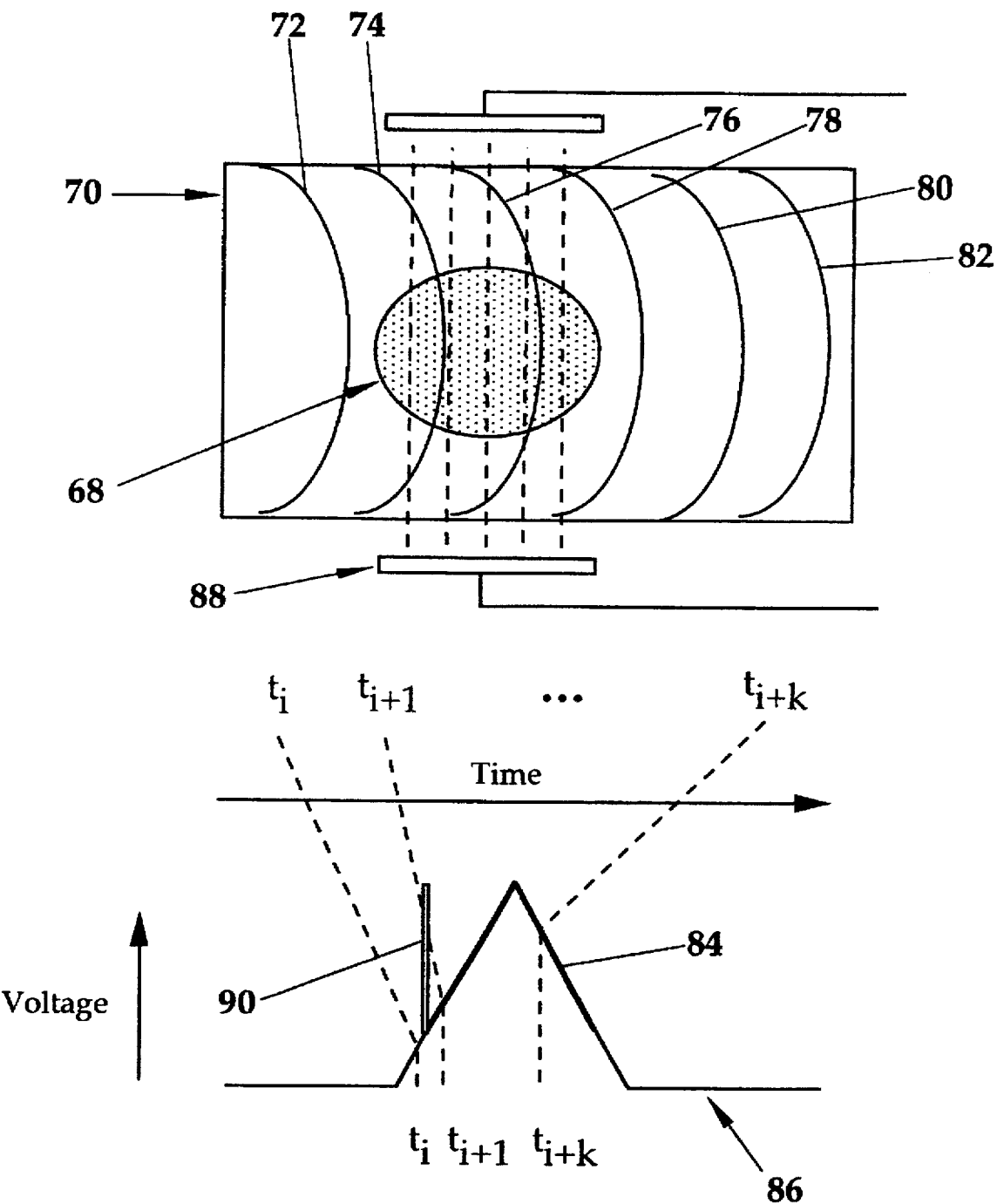
FIG. 3 illustrates the effects of active facilitation regarding its ability to facilitate the time course of a portion of an electrical wave front across compromised or depressed myocardial tissue, and the corresponding contribution of this portion of the wave front to a R-wave of a cardiac cycle.

FIG. 3 illustrates the effects of active facilitation (AF). At the moment the wave front 74 enters the area of the depressed tissue 68, a current pulse 88 is delivered across the area as shown. The results of Antzelevitch et al. teach that current pulse 88 changes the manner in which the wave front depicted at 72, 74, 76, 78, 80, and 82 crosses depressed tissue 68. Depending on the time and the voltage level 90, which is directly proportional to the current level in this apparatus, the pulse 88 actively facilitates or inhibits the conduction across the section 68 of tissue 70. The resulting voltage changes for a cardiac cycle 86 impact the R-wave morphology 84, and are recorded in the ECG. Therefore, by delivering a current pulse 88 across tissue 70 at different times and at different levels of current from one cardiac cycle to the next, the voltage signals recorded by the ECG are actively altered from one cardiac cycle to the next.

Figure 4:
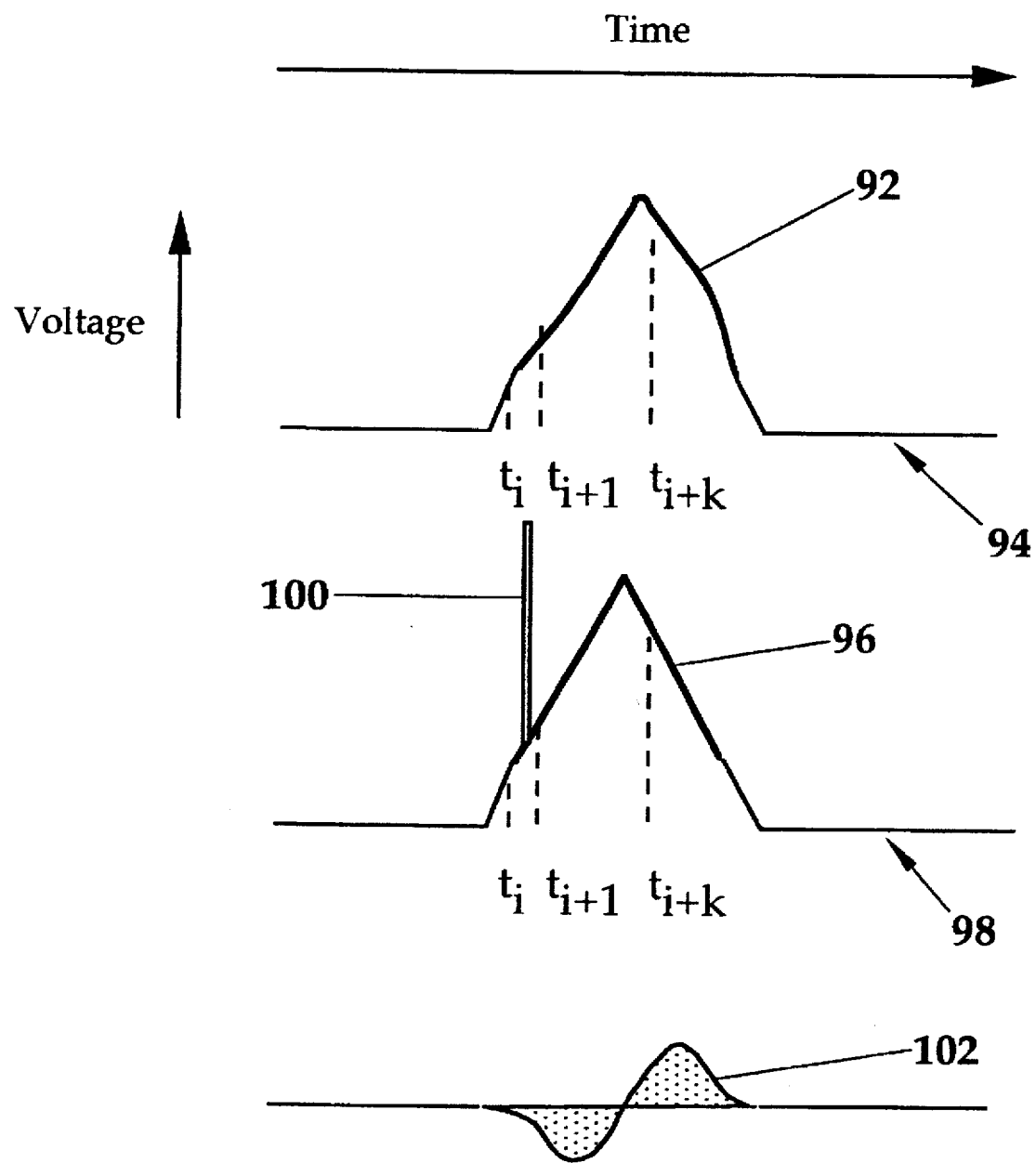
FIG. 4 shows a time-wise aligned pair of R-waves from adjacent cardiac cycles, in which one complex illustrates normal electrical behavior and one complex illustrates the effects of facilitation, and the corresponding algebraic difference between the two R-waves.

FIG. 4 illustrates the changes 92 and 96 from one cardiac cycle 94 to the next 98 as seen in the recorded ECG signal. No pulse is delivered during the first cardiac cycle 94. By passing current through the heart in the form of a single, short pulse 100 during the second cardiac cycle 98, myocardial conduction is actively facilitated, producing subtle changes in an ECG signal. These possible effects of AF are discerned by observing and analyzing minute, measurable differences 102 in the recorded voltage signals of the two cardiac cycles 94 and 96. FIG. 4 shows an idealized, exaggerated response of a diseased heart.

Normal, healthy cardiac tissue is minimally affected by these small current pulses 100, and there are no significant changes in the ECG signal from one cardiac cycle 94 to the next 98. Patients with hearts that have no sections of depressed or compromised tissues have no discernible, recorded changes 102 found in their ECG signals when AF is applied in a diagnostic setting. On the other hand, those patients who suffer from malignant ventricular tachycardias or fibrillation as outcomes to chronic CAD or prior myocardial infarction are known to have compromised or depressed section of myocardium, possibly in the form of myocardial ischemia or fibrotic tissues. These patients have discernible, recorded changes 102 in their ECG when diagnostic levels of AF 100 are applied across their heart. Measurable amounts of subtle changes 102 due to AF 100 serve as important markers from which physicians can derive a patient's level of risk for SCD. Therefore, the present invention automatically and adaptively delivers a carefully timed burst of current 100 across a patient's heart as a means to implement AF, monitors and evaluates the patient's ECG signals 94 and 98 for discernible, recorded changes 102 in these ECG signals due to current burst 100, and computes, displays and outputs a plurality of recorded changes 102 in the form of instability waveforms and indices.

Description of the Principle Physical Elements

Figure 5:
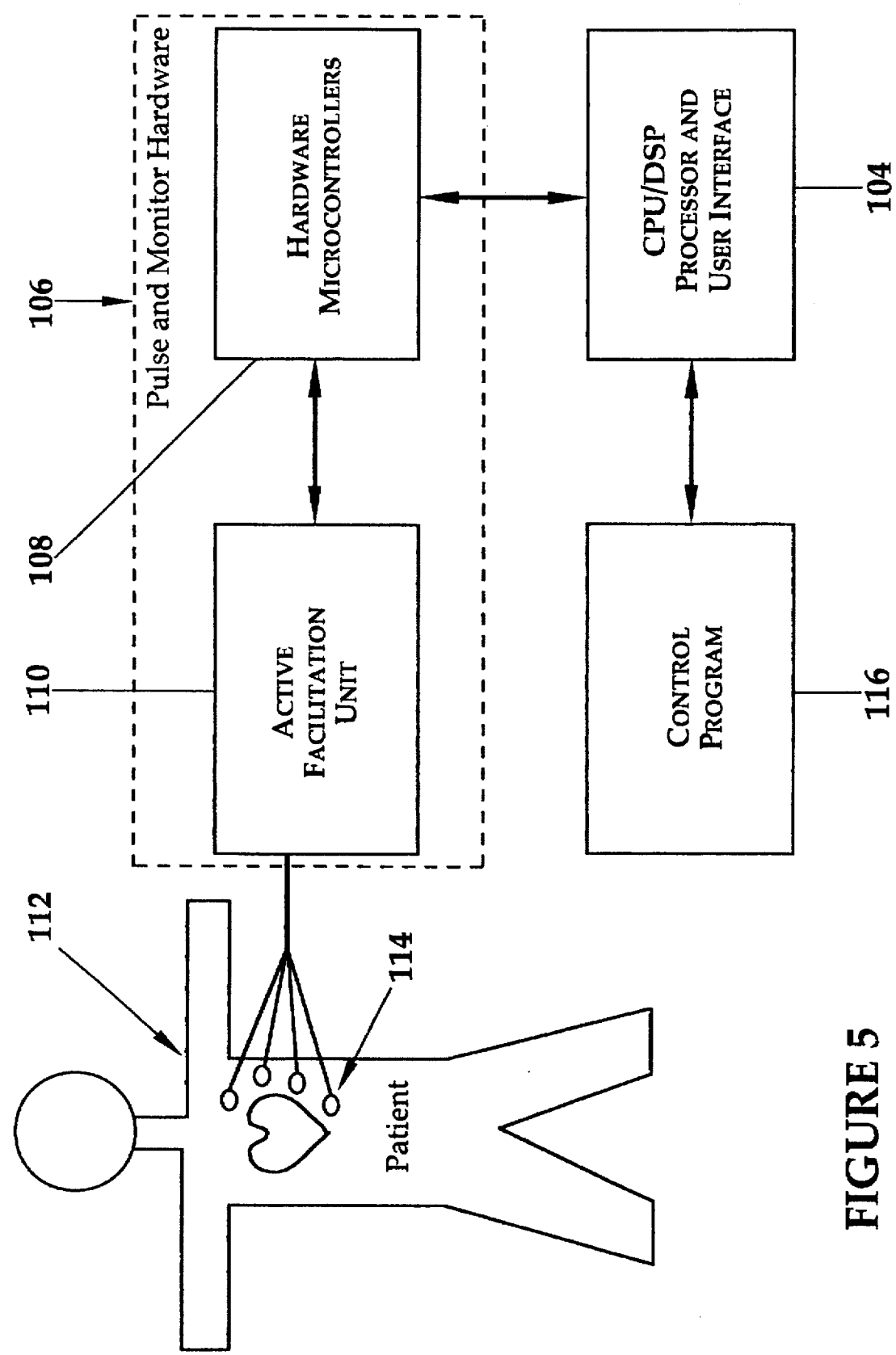
FIG. 5 is an overview of the invention's primary hardware and software elements of the invention and their interconnection for its operation in the diagnosis of a patient's myocardial electrical instability.

FIG. 5 illustrates the principle physical elements of the invention. The four elements that comprise the invention are a high performance computer 104, a control program 116, a microcontroller board 108, and an active facilitation (AF) unit 110. The control program 116 operates the apparatus, interacting with a physician or trained operator and automatically controlling the hardware AF unit 110 via the hardware microcontroller board 108. The hardware microcontroller board 108 resides in the computer 104 and controls and synchronizes the hardware subsystems that comprise the AF unit 110. The AF unit 110 delivers groups of shaped, facilitating pulses to a patient 112 and acquires a plurality high-fidelity ECG signals from the patient 112 for an ongoing, real-time evaluation of the active facilitation. The AF unit 110 connects to the patient 112 via electrodes 114. The AF unit 110 utilizes these electrodes 114 to deliver the minute amounts of current across a patient's heart and to acquire the plurality of high-fidelity ECG signals. The AF unit 110 and the hardware microcontroller board 108 comprise the pulse and monitor hardware 106.

To operate the apparatus, a physician or a trained operator first hooks the AF unit 110 comprising a pulse delivery subsystem and an ECG to a patient 112 via electrodes 114. The physician then initiates a diagnostic test by starting the control program 116. The control program 116 interrogates the physician for parameter values that tell the control program 116 how to structure the delivery of pulses and the monitoring of ECG signals. The parameters are called space structuring parameters because they define a parameter-outcome space. If indicated by the physician or operator, the control program 116 can also start a diagnostic test using a set of default space structuring parameter values or a set of space structuring parameter values that were saved from a previous time that the apparatus was operated. The control program 116 starts a diagnostic test, and no further physician or operator intervention is required to complete the testing portion of the invention's operation. The invention proceeds automatically, but it can be halted at any time. The control program 116 can also be temporarily overridden by the physician and operated manually from time to time if so desired. After operating the apparatus manually, the physician returns control of the test procedure to the control program 116. The control program 116 is a software program that implements the methods and apparatus as described in detail below.

The invention provides a means to effectively search for and discover pathological, electrical characteristics of the heart by utilizing the delivery and monitoring of one or more facilitating pulses over a plurality of cardiac cycles. The search process is an adaptive process. The search process decides how to construct a new pulse sequence for a group of cardiac cycles based on its discovery of changes in the ECG signals of a prior group of cardiac cycles due to a prior pulse sequence. This adaptive search and discover procedure (ASDP) is a means to control the design and delivery of pulse sequences from one group of cardiac cycles to the next. This adaptive search procedure is a sophisticated combination of software and hardware elements that are described in detail below. With these software and hardware elements, the invention effectively carries out the diagnostic procedure for the determination of a patient's likelihood of SCD by computing one or more indices for myocardial electrical instability. With these software and hardware elements, the invention adaptively probes the heart electrically for the effects of disease.

A process of pulsing the heart with small amounts of current over a plurality of cardiac cycles and monitoring the electrical activity of the heart for effects manifested in the ECG signals is a process that we call active facilitation (AF). Hereinafter, a pulse sequence shall mean a delivery of specific pulses across a heart together with a synchronized acquisition of ECG signals associated with the group of cardiac cycles affected by the pulsing. Equivalently, a pulse sequence shall also mean a set of instructions regarding a delivery of a group of pulses over a period of time comprising one or more cardiac cycles. Equivalently, a pulse sequence shall also mean an AF parameter point in a parameter outcome space utilized by the ASDP that summarizes the instructions and descriptions for the delivery of a pulse sequence.

The invention specifically operates within the range of the R-waves of a cardiac cycle. It is well-known that a pulse can induce VF if the pulse has certain voltage, current, and waveform characteristics and is delivered during a vulnerable phase of the cardiac cycle. The vulnerable phase of a cardiac cycle coincides with the T-wave. Therefore, the operation of the ASDP and the delivery characteristics of a current pulse are constrained to regions of a cardiac cycle associated with the R-wave to safeguard a patient from induced VF.

Description of the Software Elements

Figure 6:
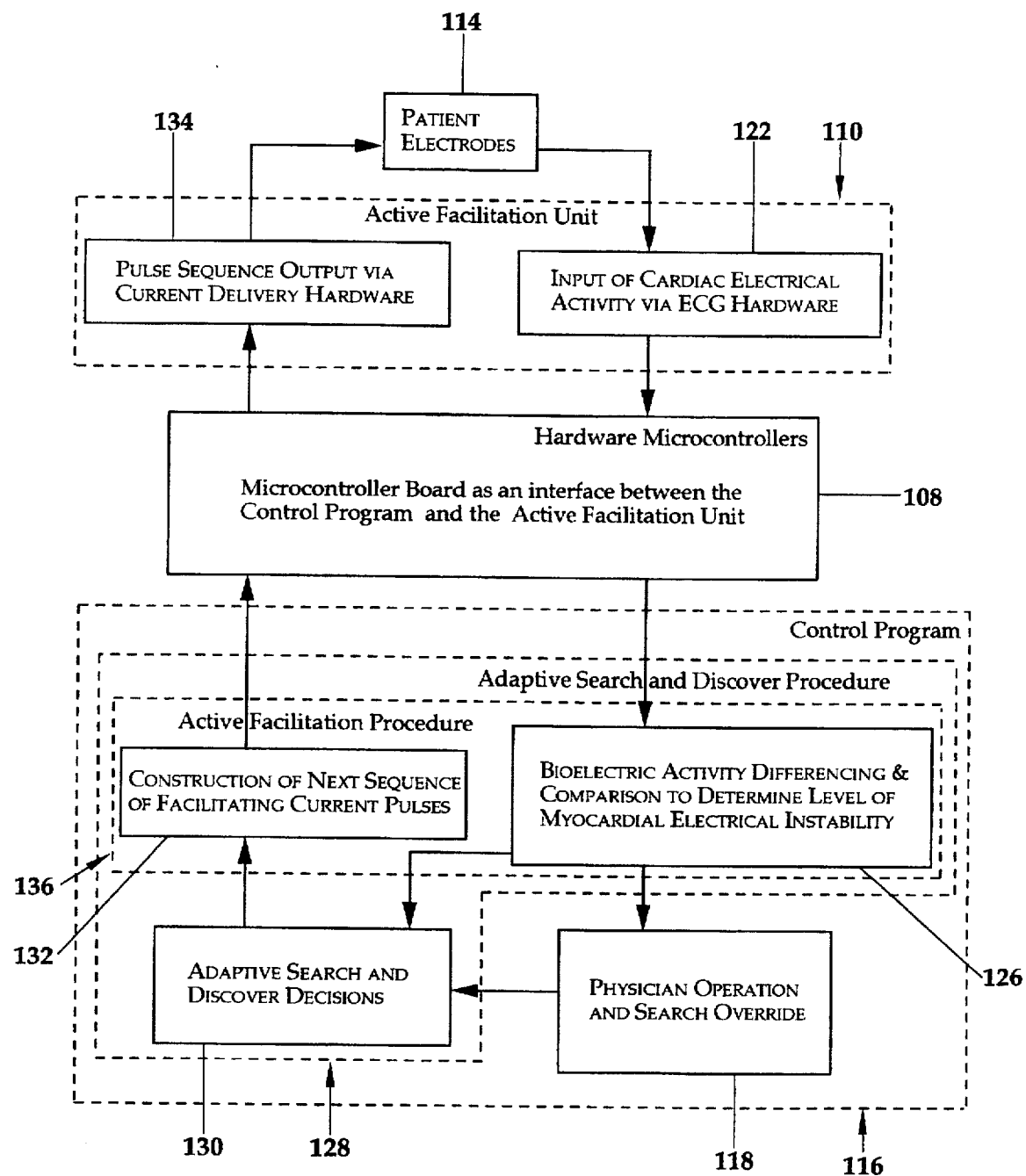
FIG. 6 is an overview of the adaptive search and discovery procedure implemented by the control program, the hardware microcontroller, and the active facilitation unit.

FIG. 6 illustrates the top-level operation of the invention's control program 116 with its automated test and evaluation loop, as overseen by a physician or a trained operator 118. While the apparatus is attached to a patient via the AF electrodes 114, the invention's control program 116 automatically alternates between placing small amounts of current pulses through a patient's heart and recording the heart's response to these small current pulses.

The heart's response is acquired by measuring the surface voltage using a digitizing ECG hardware subsystem 122, 108. The ECG subsystem 122, 108 senses the electrical activity of the heart by means of the AF electrodes 114, and provides a digitized form of the analog voltage signal that is sensed. The ECG subsystem 122, 108 collects a plurality of ECG signals before and after the delivery of a facilitating pulse. The control program 116 uses the ECG signals to construct a "dynamic contrast image" in the form of a difference waveform and index 126, compares the index to a set of previously computed indices 126, presents the comparison results to the physician 118 and stores these results for later output to a printer 118. Therefore, a patient's ECG signals are used first to monitor and evaluate the electrical effects of the delivered sequence of pulses on the patient's heart, and second to construct waveforms and indices that guide the ASDP 128 in making decisions regarding the design and implementation of a new sequence of pulses for a new diagnostic step of the testing procedure.

The control program 116 next automatically decides what new sequence of pulses to implement 130 to continue its assessment of the patient's level of myocardial electrical instability. In accordance with its decision 130, the apparatus then constructs a new sequence of pulses 132 to output to the patient across a group of cardiac cycles, and delivers the new sequence of facilitating pulses 108, 134 through the patient's heart. This output of pulses 108, 134 and the input of ECG signals 122, 108 operated synchronously, automatically, adaptively, and continuously by the control program 116 and the ASDP 128 until such time that the ASDP 128 has determined a maximal level of electrical instability possible, or halts the process to guard against unsafe operation, or is halted by the physician or operator 118.

To best understand the operation of the control program 116 and its software elements, we enumerate the five major software subsystems, or procedures, in detail. The first software procedure is the control program 116, that interacts with a physician 118 to operate the invention and to control an adaptive search and discovery procedure 128. The control program 116 has been previously described. The second software procedure is the adaptive search and discovery procedure (ASDP) 128 that utilizes a nonlinear optimization method 130, called the simplex method, to maximize the output of an objective function. The objective function is called the AF procedure 136. The input to the AF procedure 136 is an AF parameter point and the output from the AF procedure is a computed instability index. The AF procedure 136 transforms an AF parameter point into an instability index, which it then sends back to the simplex method 130 for further decision-making. The AF procedure 136 performs two major functions to construct an instability index related to an input AF parameter point. The first major function of the AF procedure is also the third software procedure, and is called the AF control element 132. The AF control element 132 transforms an AF parameter point into specific hardware instructions regarding the delivery of pulse sequences and the monitoring of ECG signals, and sends these instructions to the hardware controller board 108, thereby initiating AF. The second major function of the AF procedure is also the fourth software procedure, and is called the AF analysis element 126. The AF analysis element 126 evaluates monitored ECG signals and computes an instability index. The fifth software procedure comprises the embedded microcontroller codes 108 that implement the instructions for an AF pulse sequence.

Figure 7:
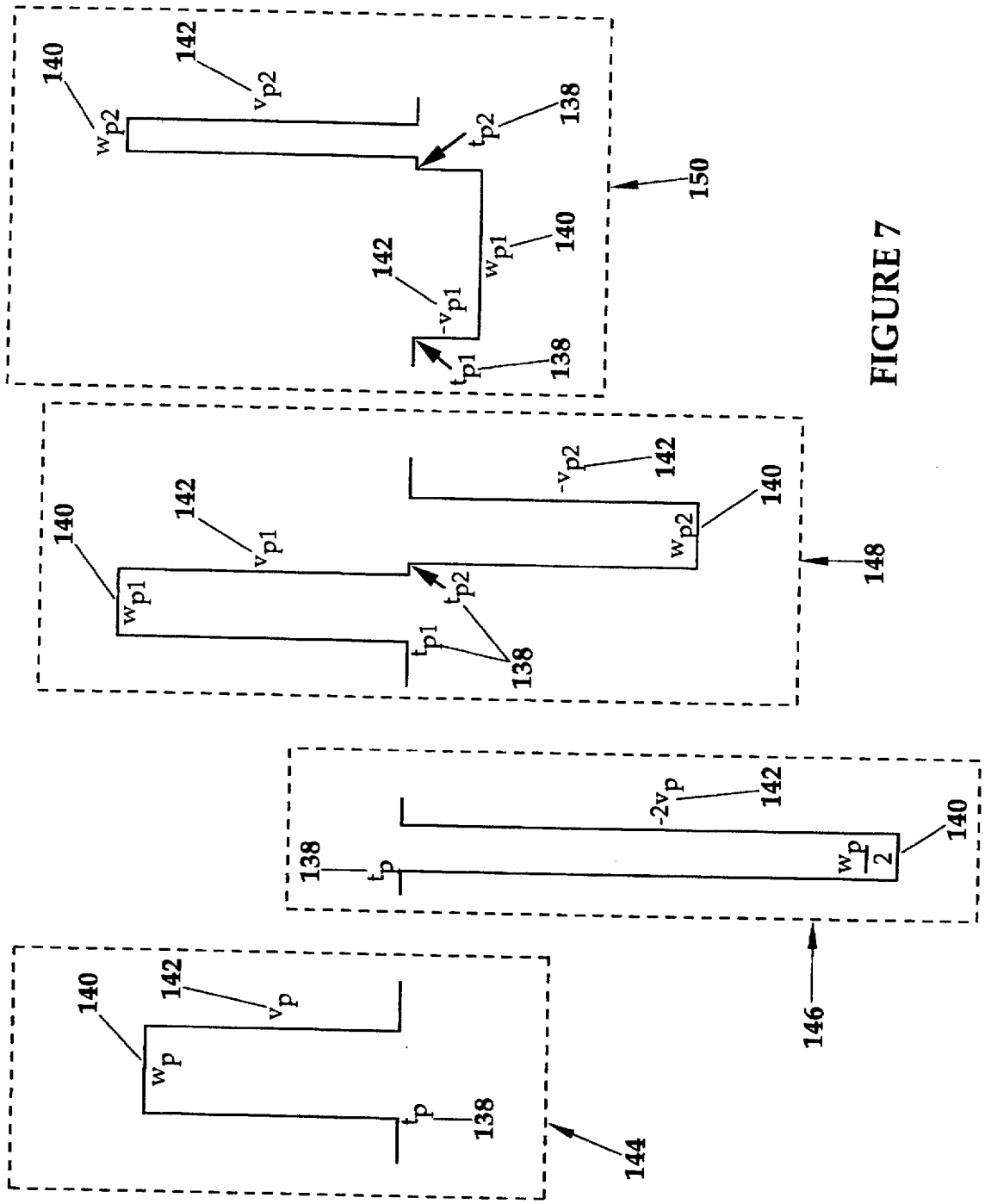
FIG. 7 illustrates the pulse shapes and the corresponding characterizing pulse parameters of current pulses delivered across a patient's chest and through the heart.

A parameter-outcome space is composed of AF parameter points and provides the ASDP, the simplex method, and the AF procedure with a compact descriptor that summarizes the instructions for a pulse sequence. An AF parameter point comprises a list of parameters that define a pulse sequence. The first parameter is the number N of cardiac cycles over which a set of pulses are applied, thereby implicitly describing the length of time that the apparatus shall apply a pulse sequence. Following this parameter are N cardiac cycle records, one record for each cardiac cycle. Each cardiac cycle record describes a unique pulse pattern for that cycle. The first parameter of a cardiac cycle record is the number P of pulses to be delivered during the cardiac cycle. Following this parameter are P pulse records, one record for each pulse. As illustrated in FIG. 7, each pulse record comprises a list of characterizing parameters that designate the starting time position 138 ($t_p$) for the pulse in the cardiac cycle, the width 140 ($w_p$) of the pulse, the polarity or sign ($s_p$) of the pulse, the voltage amplitude ($v_p$) of the pulse, and a list of electrode pairs utilized to deliver the pulse. The polarity and the voltage amplitude parameters are incorporated into a single number 142 in which the magnitude of the number represents the amplitude and the sign of the number represents the polarity. The list of electrode pairs is encoded in a single digital word.

Following the cardiac cycle records are the parameters that describe the monitoring characteristics of the pulse sequence. The first monitoring parameter is the cut-off frequency for the analog, high-pass filter and the second monitoring parameter is the cut-off frequency for the analog, low-pass filter. The third monitoring parameter is a list of electrodes utilized to monitor the pulse. The list of monitoring electrodes is encoded in a single digital word and has a similar encoding scheme to that used for the pulsing electrodes.

FIG. 7 illustrates four pulses. The first pulse 144 is a monophasic pulse delivered with a positive polarity. The second pulse 146 is a monophasic pulse delivered with a negative polarity, one-half the pulse width, and twice the voltage amplitude as the first pulse. The third 148 and fourth 150 pulses are biphasic pulses. A biphasic pulse is constructed by delivering two monophasic pulses of opposite polarity adjacent to one another. The third pulse 148 illustrates a biphasic pulse in which the first phase of the pulse has the same pulse width and voltage amplitude as the second phase. The fourth pulse 150 illustrates a biphasic pulse in which the first phase has negative polarity, is much wider, and has one fourth the voltage amplitude compared to the second phase.

An AF parameter point is divided into two parts. The first part of an AF parameter point comprises the number N of cardiac cycles for a pulse sequence and the number P of pulses to be delivered in each cycle. These two parameters may be adjusted at the start of a diagnostic test, but remain fixed during the operation of the diagnostic test. At the end of the diagnostic test, the two parameters may again be adjusted to other values for a second test. The second part of an AF parameter point comprises the list of pulse characterizing parameters for each pulse delivered in each cardiac cycle and the list of monitoring parameters. It is the second part of an AF parameter point that is utilized by the simplex method to search for a maximal value of electrical instability during a diagnostic test. Fixing the number of cardiac cycles and the number of pulses per cycle places an upper bound on the complexity of a pulse sequence but does not limit the ability of the apparatus. Fixing these parameters lowers the overall possible dimension for a search space, thereby reducing the overall time of operation of the invention without restricting the ability of the apparatus to successfully perform a diagnostic test. Indeed, designating a cardiac cycle to receive a fixed number of current pulses does not restrict the freedom of the searching method to choose a lesser number of pulses to deliver during the cycle. The searching method chooses not to deliver a pulse during a cycle, for example, by choosing the amplitude of the pulse to be zero.

The second software procedure, the ASDP, comprises a procedure that oversees the operation of a non-linear function-optimizing algorithm as its search method. Specifically, the invention utilizes the simplex method as developed by Spendley, Hext, and Himsworth (*Technometrics* 1962; 4: 441) and improved by Nelder and Mead (*Computer Journal* 1965; 7: 308–313). The simplex method provides a method of searching through any well-defined space of descriptors to a problem, evaluating an objective function that characterizes the problem, and finding local or global maximal (or minimal) values to this function. The global maximum provides a best solution to the problem and depends on how the objective function is defined. The simplex method is well-known to those skilled in the art of nonlinear optimization and the specific details regarding the simplex method and its various implementations will not be recited here. The simplex method is completely described and implemented, for example, in the following references: Press W H, Teukolsky S A, Vetterling W T, Flannery B P, *Numerical Recipes in FORTRAN*, $2^{nd}$ Edition, Cambridge University Press, 1992, and Nash J C, *Compact Numerical Methods for Computers*, $2^{nd}$ Edition, Adam Hilger Press, 1990.

The invention utilizes the simplex method as the central element in the ASDP. The simplex method searches through a space of pulse sequence descriptors for AF, the AF parameter points, to find the greatest changes in myocardial electrical activity of a patient. The simplex method selects a new AF parameter point with each loop through its searching algorithm. It inputs this point to the AF procedure, and the AF procedure outputs a corresponding instability index. If the index is not a maximal index, the simplex method picks a new AF parameter point and proceeds through its searching strategy again. In this manner the simplex method creates an "instability surface" that describes the condition of a patient's heart. The instability surface is flat and without many "valleys" or "hills" for a patient with no dynamical or structural heart conditions that can be discerned with AF. On the other hand, the instability surface will have many such "valleys" and "hills" for a patient with heart disease that is manifested by electrical instability. Measurements on the instability surface of a patient with a diseased heart provides an accurate picture of how the heart is affected by disease and by how much.

An important element of the simplex method is that its searching strategy determines the maximal values for the instability surface by constructing and evaluating only a small portion of the total surface. The simplex method is a non-linear optimization technique that determines local or global maximums without actually constructing the instability surface for all possible descriptors in the search space. An exhaustive searching process would be prohibitive and impossible to implement in the short period of time needed to test a patient.

Figure 8:
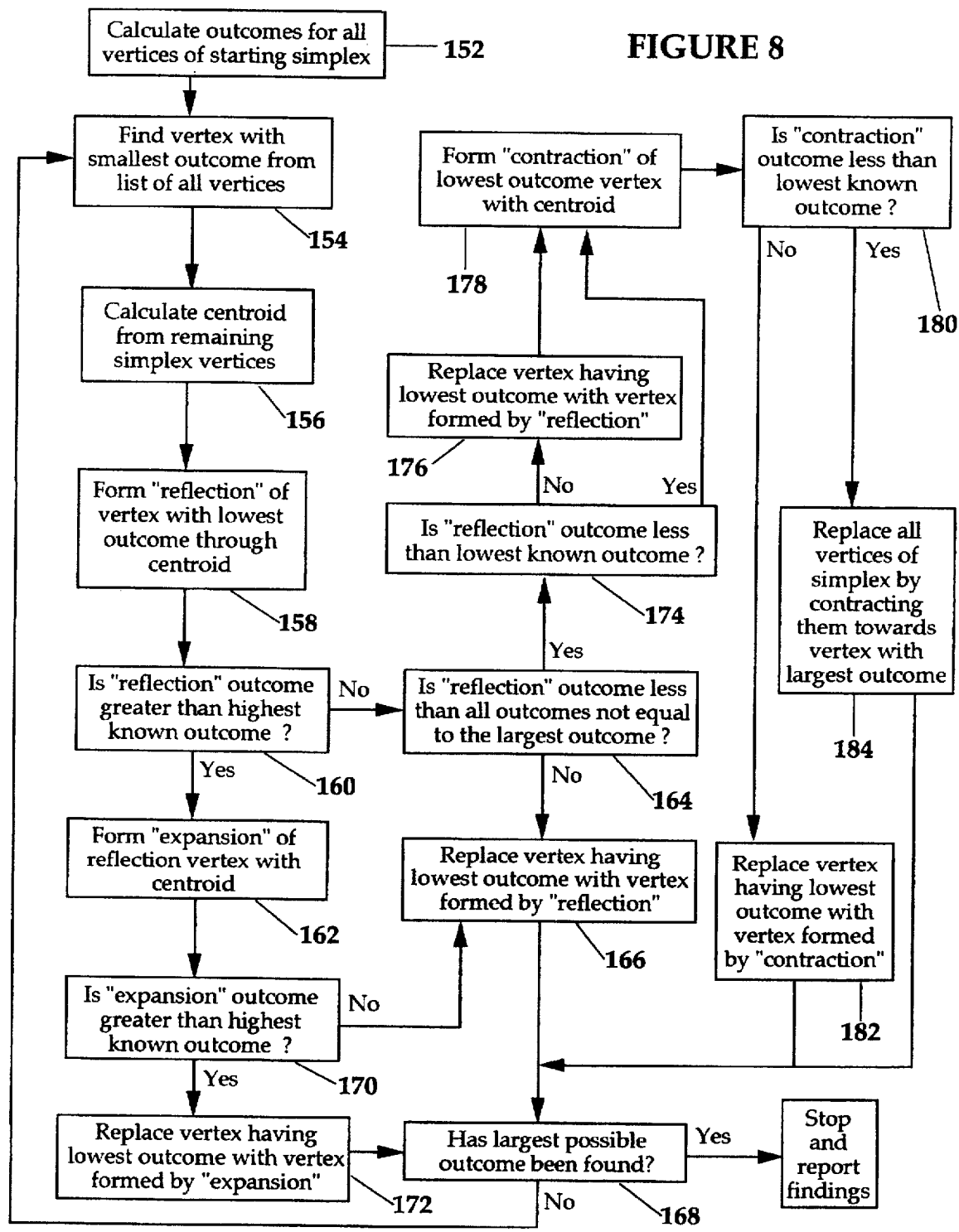
FIG. 8 is a top-level flowchart of an algorithm that implements the simplex searching method.

FIG. 8 shows a top-level flowchart of an algorithm that implements the simplex method. The simplex method starts by calculating an outcome for each vertex of a starting simplex 152. In the preferred embodiments of the invention, a starting simplex is provided to the simplex method by the ASDP. The term "vertex" is a word to describe an AF parameter point in a parameter-outcome space. An outcome for a vertex is calculated by evaluating an objective function with the vertex as input. In the preferred embodiments of the invention, an objective function is provided to the simplex method by the ASDP and is called the AF procedure. The simplex initiates a process of modifying the initial simplex by adding and subtracting vertices according to results from comparing the vertices' outcomes.

A vertex is determined that has the smallest outcome 154 and the simplex method computes a centroid vertex utilizing the remaining vertices 156. The simplex method forms a reflection vertex utilizing the smallest outcome vertex and the centroid 158 and calculates the outcome of this reflection vertex utilizing the AF procedure. If the reflection outcome is greater than the largest outcome for the vertices of the simplex 160, the simplex method forms an expansion vertex utilizing the reflection vertex and the centroid 162 and calculates the outcome of this expansion vertex utilizing the AF procedure. Otherwise, if the reflection outcome is greater than any other vertex outcome 164, the simplex method replaces the lowest outcome vertex with the reflection vertex 166, and tests the stopping criteria 168. If the expansion outcome is greater than the largest outcome for the vertices of the simplex 170, the simplex method replaces the lowest outcome vertex with the expansion vertex 172, and tests the stopping criteria 168. Otherwise, the simplex method replaces the lowest outcome vertex with the reflection vertex 166, and tests the stopping criteria 168. Otherwise, the reflection outcome is less than all vertex outcomes 164, except perhaps the lowest outcome 174 and 176. The simplex method proceeds to contract the simplex to find a replacement vertex for the lowest outcome vertex 178. If the contraction vertex can not replace the lowest outcome vertex 180 and 182, the simplex method contracts the entire simplex 184. At the end of the contraction steps 178, 180, 182, and 184 the simplex method tests the stopping criteria 168.

The stopping criteria 168 determines when the simplex method stops searching the AF parameter-outcome space for a maximum instability index. The stopping criteria 168 are a set of rules that decide whether a maximum index has been discovered. The invention utilizing a stopping criteria 168 that keeps the simplex from becoming too small in relation to the curvature of the instability surface. As a first rule, the simplex method stops its search when the standard error of each vertex outcome is less than a predetermined value. As illustrated in FIG. 8, the simplex contracts 178, 180, 182, and 184 as the method centers this simplex about a maximum outcome. This stopping rule bounds the minimum size of the simplex in relation to the curvature of the instability surface. The rule controls the amount of time that a patient is tested during a single search for electrical instability. The remaining stopping rules relate to the kinds of abnormal electrical morphologies that are monitored during a pulse sequence. For example, one rule states that the invention shall stop a search if a predetermined number of ectopic cardiac cycles occur during a pulse sequence.

Each time the ASDP is initiated by the control program, the ASDP constructs a starting simplex and passes this simplex to the simplex method. The starting simplex comprises a set of independent AF parameter points that represent a set of pulse sequences. The ASDP constructs these AF parameter points so that no one point can be written as a linear combination of the remaining points. The construction guarantees that the starting simplex spans the AF parameter-outcome space.

Figure 9:
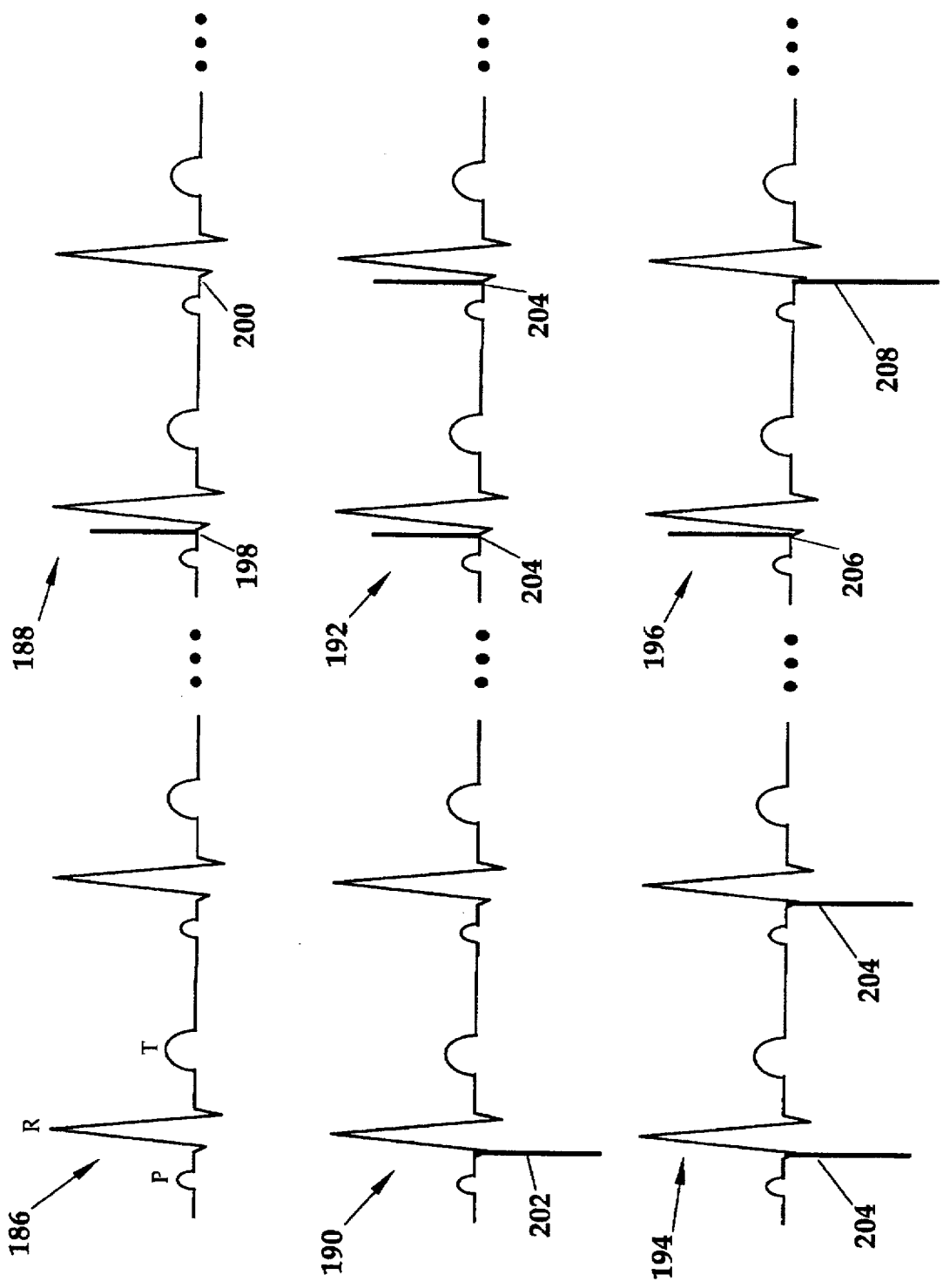
FIG. 9 shows a group of pulse sequences that illustrates the implementation of an 11 dimensional search space used by the simplex method and that are applied to a patient by the apparatus during a diagnostic test.

FIG. 9 illustrates a plurality of pulse sequences for an instantiation of the invention. An instantiation of the invention occurs each time a diagnostic test is begun. To instantiate the apparatus, the control program and its ASDP configure the apparatus for a specific search space structure defined by a set of input space structuring parameters. In this example, the ASDP uses a set of space structuring parameters to initiate a diagnostic test that uses a pulse sequence having 2 cardiac cycles and having up to 1 pulse delivered in each cardiac cycle. The first pulse sequence 186 illustrates a null pulse sequence. A null pulse sequence is one with all its pulses having zero amplitude. The second pulse sequence 188 illustrates a sequence with a pulse during the first cardiac cycle 198 and no pulse during the second cardiac cycle 200. The third pulse sequence 190 illustrates the prior sequence 188 with a polarity reversal 202 for the pulse. The fourth 192 and fifth 194 pulse sequences illustrate pulse sequences with the same pulse pair 204 applied to a cardiac cycle pair, but with opposing polarities 204. The sixth pulse sequence 196 illustrates a sequence having a second pulse 208 similar in position and amplitude but with opposite polarity to a first pulse 206. Each of these pulse sequences is defined by a unique AF parameter point.

The ASDP configures the search space illustrated by FIG. 9 as an 11 dimensional space and a simplex in this space has 12 AF parameter points as its vertices. To initiate a search with a starting simplex, the ASDP chooses an AF parameter point $AF_0$ that represents a pulse sequence that spans 2 cardiac cycles, delivers no pulses, and monitors its application with wideband ECG signals 186. The ASDP takes the other 11 AF parameter points to be the vectors $[AF_0+(\lambda \cdot e_i)]$, where the $e_i$'s are the 11 unit vectors for the search space and $\lambda$ is a predetermined characteristic length scaling value.

Figure 10:
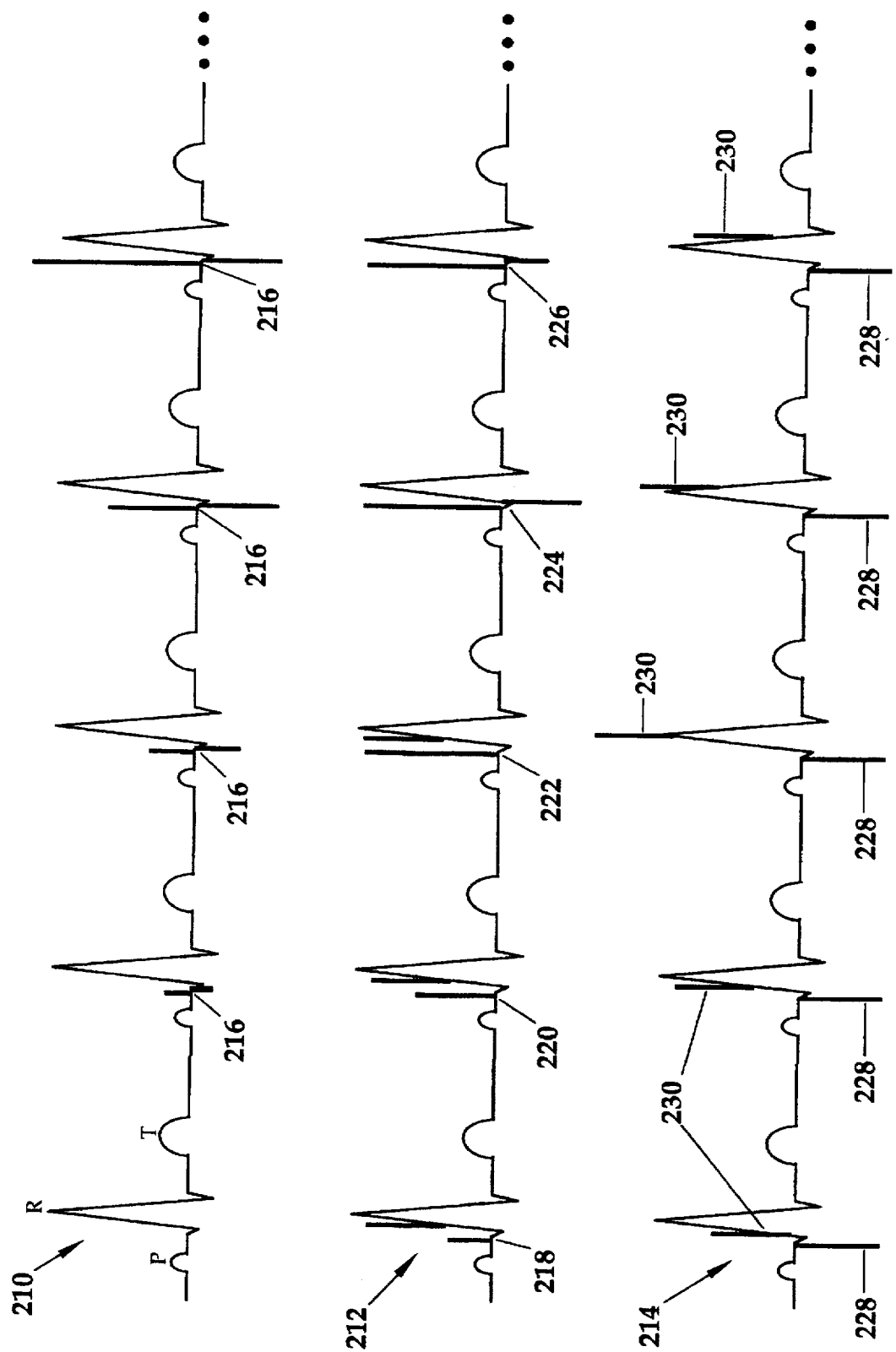
FIG. 10 shows a group of pulse sequences that illustrates the implementation of a 43 dimensional search space used by the simplex method and that are applied to a patient by the apparatus during a diagnostic test.

FIG. 10 illustrates a plurality of pulse sequences for a second instantiation of the invention. In this example, the ASDP uses a set of space structuring parameters to initiate a diagnostic test that applies a pulse sequence having 5 cardiac cycles and having up to 2 pulses delivered in each cardiac cycle. The first pulse sequence 210 illustrates a cardiac cycle sequence with a biphasic pulse 216 with ever increasing phase amplitudes delivered at the start of each cardiac cycle. A biphasic pulse 216 is formed by placing two monophasic pulses of opposite polarity in close proximity to one another. The second and third pulse sequences 212 and 214 further illustrate the flexibility and adaptive nature of the simplex method. The second pulse sequence 212 illustrates a sequence with three, fixed position, amplitude increasing, monophasic pairs 218, 220, and 222 followed by two, decreasing amplitude, biphasic pulses 224 and 226. The third pulse sequence 214 illustrates a sequence with a fixed position, fixed amplitude, negative polarity pulse 228 for a first pulse in each cardiac cycle. The second pulse 230 in this sequence migrates from the start of an R-wave to the end of an R-wave. Each of these pulse sequences is defined by a unique AF parameter point.

The ASDP configures the search space illustrated by FIG. 10 as a 43 dimensional space and a simplex in this space has 44 AF parameter points as its vertices. To initiate a search with a starting simplex, the ASDP chooses an AF parameter point $AF_0$ that represents a pulse sequence that spans 5 cardiac cycles, delivers no pulses, and monitors its application with wideband ECG signals. The ASDP takes the other 43 AF parameter points to be the vectors $[AF_0+(\lambda \cdot e_i)]$, where the $e_i$'s are the 43 unit vectors for the search space and $\lambda$ is a predetermined characteristic length scaling value.

The application of the pulse sequences represented by the AF parameter points for the starting simplex creates a baseline of diagnostic information that comprises important operating parameters for the detection and discovery of electrical instability. Each starting simplex contains an AF parameter vertex that defines a "null" pulse sequence. The null pulse sequence is a sequence that delivers no pulses to its group of cardiac cycles at the same time it monitors these cardiac cycles with one or more wideband ECG signals. The purpose of a null pulse sequence is to appraise the associated set of cardiac cycles for a set of ECG morphology parameter values. The morphology parameters are utilized to recognize an R-wave and to extract it from a cardiac cycle monitored during any subsequent pulse sequence. These morphology parameters include the mean and standard deviation of the distance in time from one R-wave to the next, the mean and standard deviation of the width of an R-wave, the mean and standard deviation of the distance from an R-wave to a T-wave, and the mean and standard deviation of the voltage amplitude of the positive and negative peaks of an R-wave.

All known optimization methods, including the simplex method, do not guarantee that a maximal value found for an objective function is in fact a global maximum. The value is at best a local maximum which may be a global maximum. The invention therefore restarts the ASDP for another search at the end of a previous search. The ASDP initiates this next search with a new starting simplex which is constructed from the previous starting simplex. The ASDP constructs the new starting simplex by transferring a previous starting simplex to a new position in the search space by a predetermined amount of multi-dimensional translation and rotation. In this way, the ASDP performs a predetermined number of searches, or diagnostic trials, as part of a diagnostic test. In this way, the invention assures a very high probability of success that a diagnostic test will find a global maximal instability index for a patient, thereby characterizing a patient's level of myocardial electrical instability.

There are many search techniques that can provide a similar method for constructing and searching the important structures contained in the instability surface described above. The simplex method is a search technique that performs its functions without any knowledge or computation of first or second function derivatives of the objective function, such that it moves uphill with respect to the instability surface in a straightforward fashion that makes no assumptions about the objective function. For this reason, the simplex method is extremely robust. There are other methods, called direction-set methods, of which Powell's method (described in the aforementioned *Compact Numerical Methods for Computers*) is the prototype, that also do not require knowledge of function derivatives to the objective function. As will be clear to those skilled in the art regarding the implementation of the AF procedure below, function derivatives of the preferred embodiments of the AF procedure as an objective function may be difficult to determine. The simplex method overcomes this limitation.

The difficulty to develop function derivatives of a preferred embodiments of the AF procedure described below does not imply that (1) it is impossible to do so, or (2) other kinds of AF procedures that may be developed for use with the apparatus are similar in difficulty. An objective function with function derivatives can be evaluated using other derivative-based search techniques in place of the simplex method. These techniques are divided into two major method groups. The first group's methods are called conjugate gradient methods (described in *Compact Numerical Methods for Computers*), as typified by the Fletcher-Reeves algorithm and the Polak-Ribiere algorithm. The second group's methods are called quasi-Newton or variable metric methods (described in *Compact Numerical Methods for Computers*), as typified by the Davidon-Fletcher-Powell algorithm or the Boyden-Fletcher-Goldfarb-Shanno algorithm. All such methods are well known to those skilled in the art.

The third software procedure and the first major function of the AF procedure is the AF control element. The AF control element transforms an AF parameter point into two instruction packets. The first packet comprises the operating instructions to the microcontrollers that control the delivery of a pulse sequence to a patient. These operating instructions are constructed from the pulsing parameters in an AF parameter point. The second packet comprises the operating instructions to the microcontrollers that control the acquisition of the ECG signals of the cardiac cycle group over which the pulse sequence is applied. These operating instructions are constructed from the monitoring parameters in an AF parameter point. The AF control element sends these two packets of operating instructions to a master microcontroller on the microcontroller board. The microcontroller board and the AF unit together comprise the pulse and monitor hardware 106 (refer to FIG. 5). The microcontroller board comprises a group of five high-performance, microprocessor chips that are integrated together on a single board to receive and dispense control instructions that carry out the detailed hardware operations necessary to execute a pulse sequence. Each microcontroller contains an embedded assembly-language control program and data space that implements a specialized function as part of executing a pulse sequence.

The master microcontroller breaks each instruction packet into its constituent parts and transmits each constituent instruction to one or more of four slave microcontrollers simultaneously. The four slave microcontrollers are called operations microcontrollers. An operations microcontroller carries out each instruction it receives, in the order that the instruction is received, and according to its coded logic. Each slave microcontroller operates independently of the other slave operations microcontrollers. In this way, the master microcontroller transmits the operating instructions to the four operations microcontrollers so that these slave microcontrollers operate in parallel to synchronize the activity of delivering pulses across a patient's heart with the activity of collecting ECG signals for immediate monitoring and evaluation. The operational details of each microcontroller are enumerated in the hardware descriptions below.

The fourth software procedure and the second major function of the AF procedure is the AF analysis element. The AF analysis element evaluates the incoming digitized ECG signals for any effects due to AF via the delivered pulse sequence. The AF analysis element operates in parallel with the AF control element and the pulse and monitor hardware. As the collected ECG signals are stored into the memory of the computer during the delivery of the pulse sequence, the AF analysis element extracts the R-wave from each cardiac cycle involved in the pulse sequence. Each newly extracted R-wave is time-wise aligned with a prior set of extracted R-waves. The first R-wave extracted from a cardiac cycle serves as the basis to which the remaining extracted R-waves are compared for alignment. The extraction and alignment procedure automatically detects and locates an R-wave in a cardiac cycle.

Figure 11:
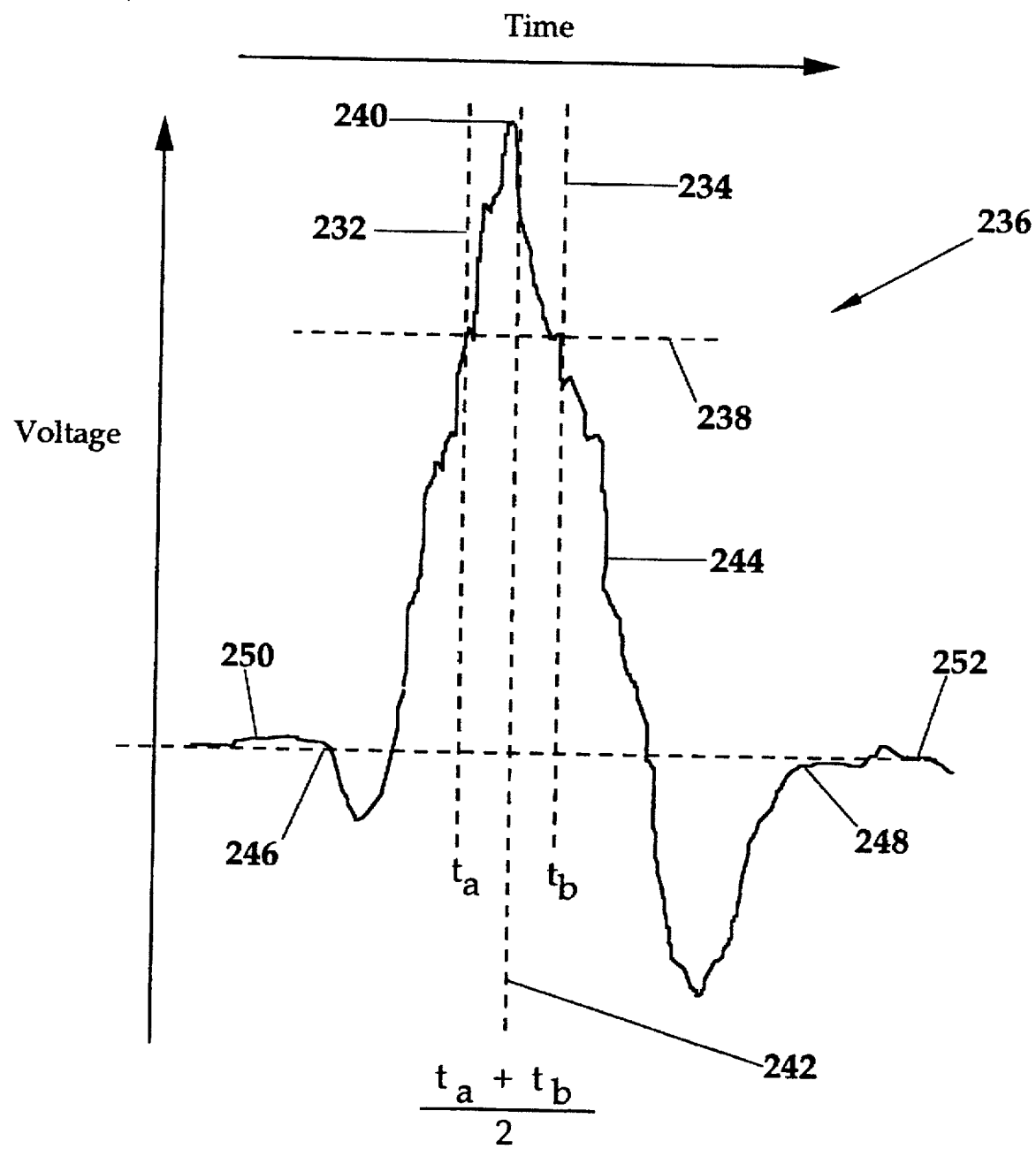
FIG. 11 illustrates a pair of threshold-determined time positions and a resulting time alignment computation using these time positions that will align an R-wave of a cardiac cycle to a plurality of other time-aligned R-waves.

The extraction and alignment procedure implements the double level detection and alignment method (*IEEE Transactions on Biomedical Engineering* 1991; 38: 571–579), and operates in several steps as illustrated in FIG. 11. First, the extraction and alignment procedure finds the largest positive peak value 232 or negative peak value 234 of the cardiac cycle 236. The procedure then selects a threshold value 238 of 0.6 times the peak value. The procedure centers a temporal window, as determined by the initial cardiac cycle detection step, at the time position of the peak value 240. Starting at the center point 240 in the window, the procedure searches backward in time for the last instance in time that the absolute value 232 of the signal values goes above the threshold level 238, denoted by $t_a$. Restarting at the center point 240, the procedure searches forward in time for the last instance in time that the absolute value 234 of the signal values goes below the threshold level 238, denoted by $t_b$. The temporal point of alignment 242 for the extracted R-wave 244 is the time equal to the average of $t_a$ and $t_b$, namely $(t_a+t_b)/2$.

Each extracted R-wave 244 is a vector of digital values of length M. The length M is determined by the extraction and alignment procedure when the first R-wave 244 of a pulse sequence is extracted from the its associated cardiac cycle. After detecting the starting point 246 and stopping point 248 of the R-wave 244 in the first cardiac cycle 236, the extraction procedure then includes a short portion 250 of the isoelectric region immediately prior to the starting point 246 of the R-wave 244 and a short portion 252 of the isoelectric region immediately following the stopping point 248 of the R-wave 244. The total length of this extracted R-wave 244 is M digital data points, and serves to determine the length of each succeeding, extracted R-wave during the time frame of the pulse sequence. For the second cardiac cycle associated with the pulse sequence, the extraction procedure detects the R-wave, aligns the R-wave to the first R-wave, and then includes a short portion of the isoelectric region at each end of this R-wave to create an R-wave vector of length M. Similarly, the extraction procedure proceeds to detect and align each R-wave from the third cardiac cycle to the $N^{th}$ (assuming $N \geq 3$), thereby producing a time-wise aligned R-wave 244 of length M for each cardiac cycle 236 associated with the pulse sequence. The time corresponding to the length M for each R-wave is called R-wave time. Each R-wave starts at R-wave time $t_1$ and ends at R-wave time $t_M$, and the digital values in an R-wave are denoted by R (j), j=1, ..., M.

Figure 12:
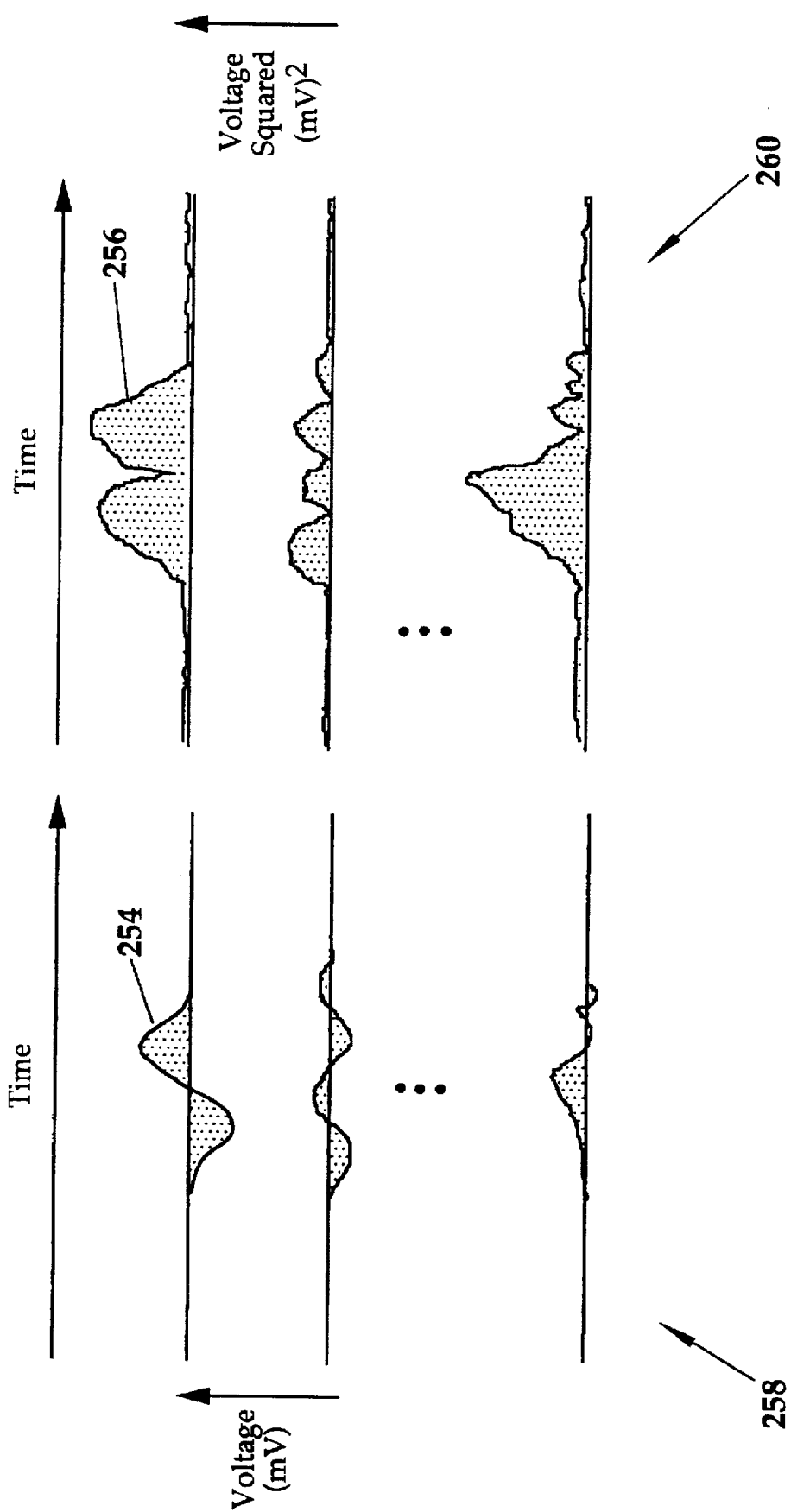
FIG. 12 shows a sequence of algebraic difference waveforms between temporally-adjacent pairs of R-waves which are constructed by subtracting one R-wave of the pair from the other, and a corresponding sequence of comparison waveforms which are constructed by squaring the algebraic difference waveforms.

At the time that an R-wave is extracted from the second cardiac cycle of the pulse sequence, it is compared to the first R-wave. FIG. 12 illustrates the algebraic difference 254 between the first extracted R-wave ($R_1$) and the second extracted R-wave ($R_2$). A comparison waveform 256 between the two R-waves is defined as a point by point squaring of the algebraic difference 254 between them. This first comparison waveform 256 is described by the formula $$C_1(j)=(R_2(j)-R_1(j))^2, j=1, \ldots, M.$$

The waveform 256 constructed by the comparison calculation is then stored in the computer's memory. The extraction of the second R-wave, its alignment to the first R-wave, the comparison calculations 254 and 256, and the storing of the comparison waveform are performed immediately following the end of the T-wave of the second cardiac cycle. The time required to perform these operations is less than 5 milliseconds.

The R-wave comparison procedure is performed immediately following the end of the T-wave for each succeeding cardiac cycle of the pulse sequence. R-wave comparisons 256 and 260 are made between the cardiac cycle currently being monitored and the cardiac cycle monitored immediately prior to the current one. There are N ($\geq 2$) cardiac cycles associated with the time frame of the pulse sequence, and there are N–1 ($\geq 1$) such comparisons 256 and 260. The associated comparison waveforms 256 and 260 are described by the formula $$C_k(j)=(R_{(k+1)}(j)-R_k(j))^2, j=1, \ldots, M,$$

where the subscript k runs from 1 to (N–1) to indicate the comparison of all temporally-adjacent pairs of R-waves. At the end of the pulse sequence there are N–1 ($\geq 1$) stored comparison waveforms 256 and 260. FIG. 12 illustrates the set of algebraic difference waveforms 254 and 258 and the comparison waveforms 256 and 260 that are constructed for each pair of temporally-adjacent, extracted R-waves.

Figure 13:
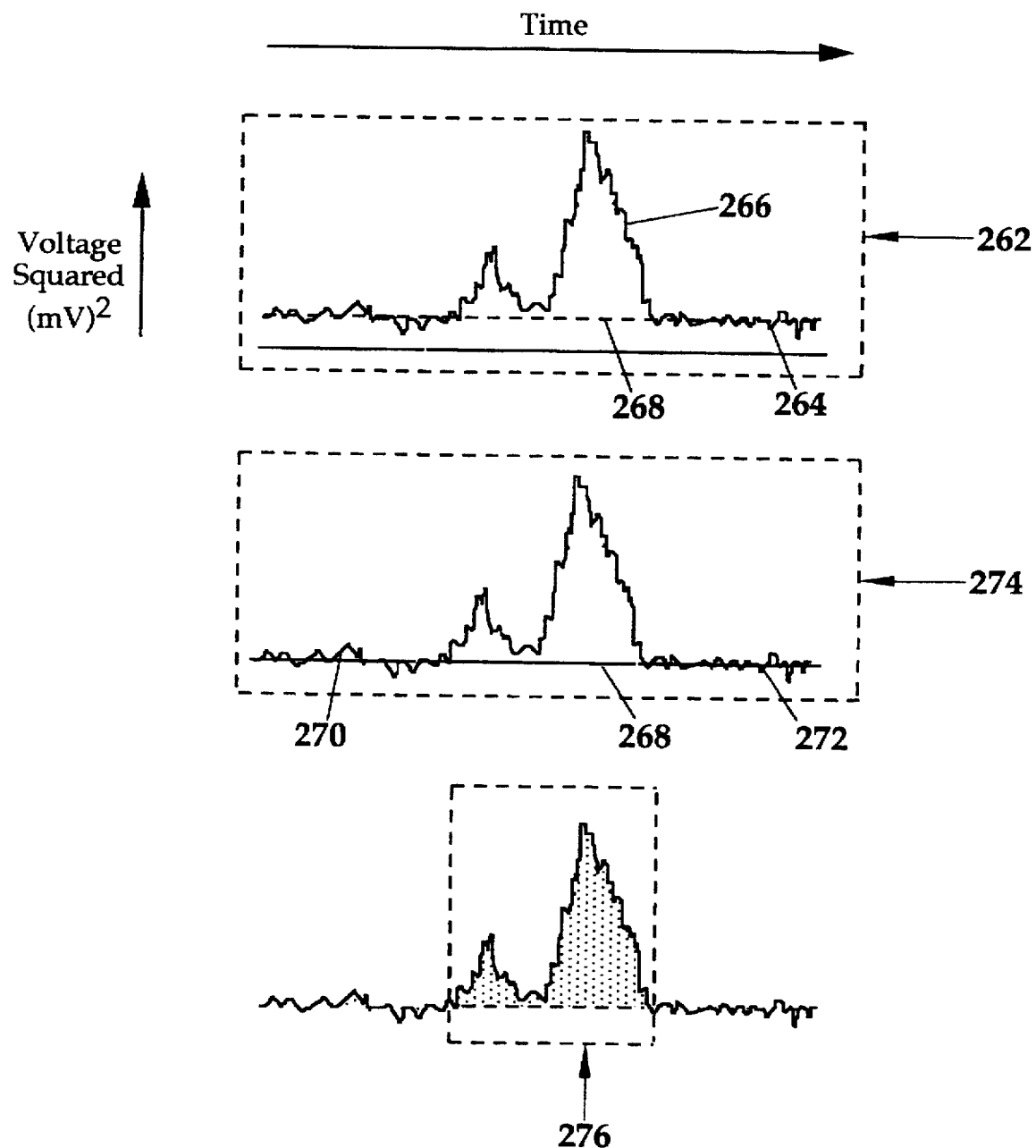
FIG. 13 shows a facilitated instability waveform before and after baseline removal, and an "area under the curve" resulting from the integration of this baseline adjusted instability waveform to provide an instability index.

Immediately following the comparison 260 of the last two temporally-adjacent cardiac cycles associated with a pulse sequence, the AF analysis element calculates a value that measures the myocardial electrical instability determined by the pulse sequence by utilizing the stored comparison waveforms, illustrated in FIG. 13. The AF analysis element constructs a myocardial electrical instability waveform 262 which is a point by point average of the comparison waveforms 256 and 260. The myocardial electrical instability waveform 262 is described by the formula $$W_{AF}(j)=(\Sigma C_k(j))/N, j=1, \ldots, M,$$

where the subscript k runs from 1 to N to indicate the average of the $j^{th}$ point in R-wave time across the set of comparison waveforms 256 and 260. Therefore, for each point in R-wave time the myocardial electrical instability waveform 262 is the Allan variance computed across the R-waves with regard to their temporal ordering in the group of cardiac cycles associated with the delivered pulse sequence. FIG. 13 illustrates the myocardial electrical instability waveform 262 that results from averaging the comparison waveforms 256 and 260.

An R-wave comprises two components, a deterministic component and a random component. The average R-wave, $R_A(j)$, over a set of R-waves, $R_k(j)$, k=1, ..., N, comprises the deterministic components that are common to each R-wave in the R-wave set. The remaining portion of an R-wave is called the noise and is described by the formula $$Noise_k(j)=(R_k(j)-R_A(j)), j=1, \ldots, M.$$

The noise represents the random component of an R-wave. The random component is defined as that part of an R-wave that is unique to the R-wave and which is not common to the set of R-waves. Specifically, the noise comprises the background noise 264, which is distributed uniformly across the R-wave, and the wideband, temporally locked or R-wave time-locked changes 266 due to the natural or facilitated myocardial electrical instability.

Three important features are present in the myocardial electrical instability waveform 262 by the very definition of calculating an instability waveform between temporally-adjacent R-wave pairs. First, the myocardial electrical instability waveform 262 extracts the random components 264 and 266 of each R-wave for the waveform, and does so without a computation of an average R-wave. Second, the independence of the background noise 264 to any particular position in R-wave time causes it to appear as a baseline 268 of the waveform 262. Third, the instability waveform 262 captures only those electrical changes that occur from one cardiac cycle to the next, thereby minimizing errors in the waveform 262 due to long-term nonstationarity of underlying physiological processes.

The AF analysis element calculates an average value B for the baseline 268 of the myocardial electrical instability waveform 262. The AF analysis element calculates the value 268 over the R-wave times that define the short portions 270 and 272 of isoelectrical regions attached to the ends of each R-wave. The AF analysis element subtracts this baseline value B 268 from the myocardial electrical instability waveform 262, to provide a waveform 274 that we call the facilitated instability waveform. The facilitated instability waveform 274 is described by the formula $$W^*_{AF}(j)=(W_{AF}(j)-B), j=1, \ldots, M.$$

The facilitated instability waveform 274 represents the subtle electrical changes that occurred from one cardiac cycle to the next during AF.

As a final computational step, the AF analysis element calculates the facilitated instability index $I_{AF}$ for the pulse sequence as a normalized area under the curve 276 represented by $W^*_{AF}$. The AF analysis element outputs the index 276 to the simplex method as the outcome of a pulse sequence. The facilitated instability index 276 is described by $$I_{AF}=(\Sigma W^*_{AF}(j))/S,$$

where the summation represents a digital integration of $W^*_{AF}$ 274 over R-wave time and S is a value computed to normalize the summation with regard to R-wave amplitude. FIG. 13 illustrates a myocardial electrical instability waveform 262 with its baseline 268 of background noise, the facilitated instability waveform 274 that results from the removal of this baseline 268, and an area under the curve 276 that measures the electrical instability derived from a pulse sequence.

The normalization parameter S is defined as an average value of the square of the peak to peak amplitude of each R-wave of the pulse sequence, and is described by the formula $$S=(\Sigma(R_{k,pp}-R_{k,np})^2)/N,$$

where the subscript k runs from 1 to N, $R_{k,pp}$ represents the positive peak value for the $k^{th}$ R-wave, and $R_{k,np}$ represents the negative peak value. S normalizes the digital integration of $W^*_{AF}$ to provide an index 276 that is compensated for the variability in R-wave amplitude from one ECG signal to another. The R-wave amplitude normalization provides facilitated instability indices 276 that are comparable when computed using different ECG signals. The normalization creates a stable index 276 from one pulse sequence to the next as computed by the AF procedure since the simplex method may choose to range across a plurality of ECG electrodes hooked to a patient during its search for myocardial electrical instability.

Figure 14:
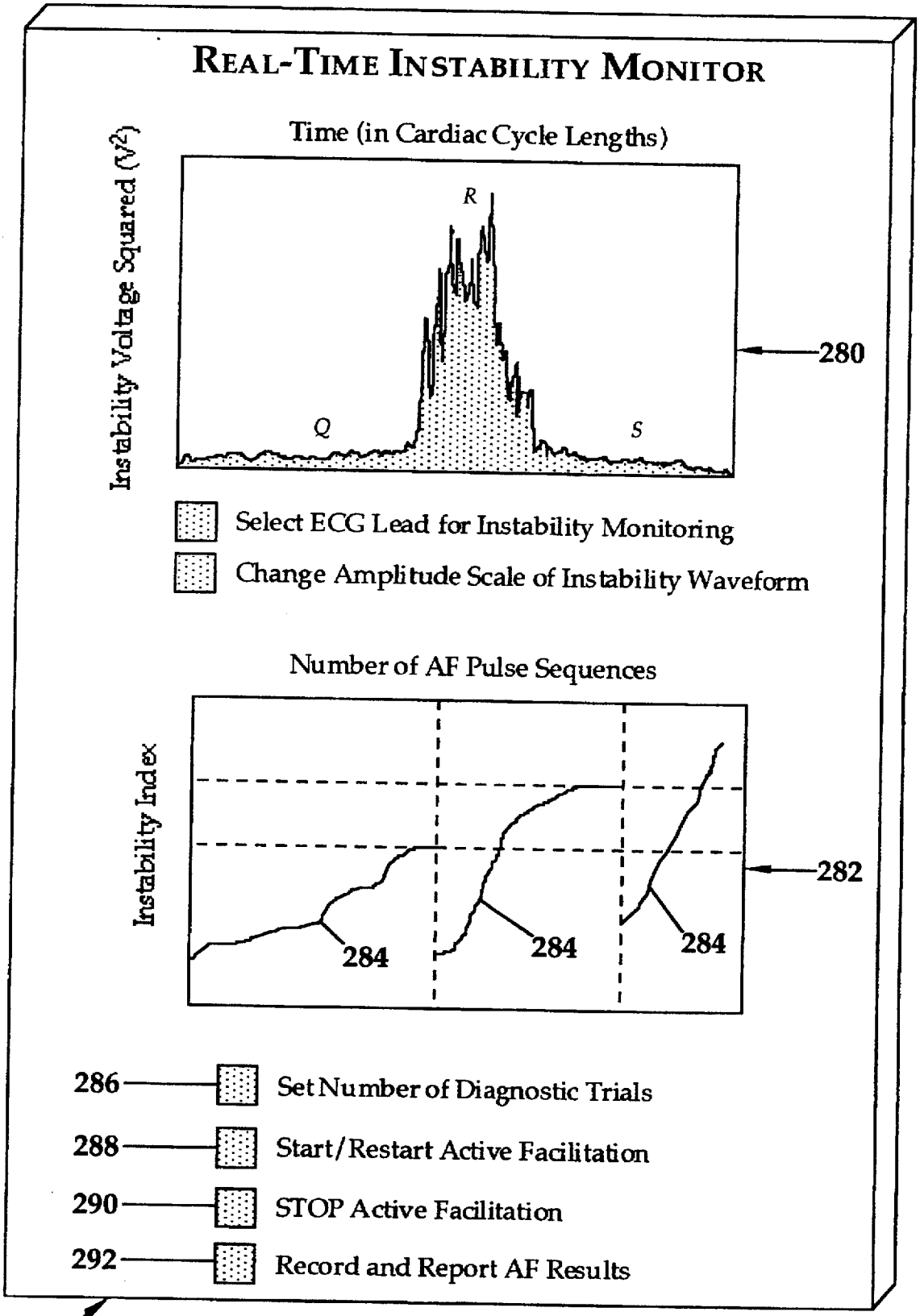
FIG. 14 illustrates the display of the monitoring and analysis results obtained during the operation of the apparatus to determine a patient's level of electrical instability via active facilitation.

In connection with the automatic and continuous computation of an instability index 276, the control program 116 operates an interactive user interface 278 illustrated in FIG. 14. The interface 278 is called the instability monitor. The interface 278 permits the physician or a trained operator to start, stop, monitor, and evaluate the progress of the control program 116 and the ASDP 128. During a diagnostic test, the control program 116 continually updates a display of the facilitated instability waveform 280 derived from each pulse sequence delivered to a patient. The control program 116 also displays the facilitated instability index 282 derived from each pulse sequence. The facilitated instability index is displayed as a function 284 of pulse sequences to provide the physician with on-going, real-time feedback regarding the progress of the ASDP 128 to diagnose a patient for electrical instability. The physician utilizes the instability waveform 280 and index information 282 to make decisions regarding the stopping, evaluating, and restarting of the ASDP. FIG. 14 illustrates the monitor for an instability waveform 280 and a plurality of instability indices 282. Immediately following a time that the AF procedure provides the simplex method with an instability waveform 274 and index 276, the simplex method provides this waveform 274 and index 276 to the control program 116. The control program 116 updates the display of the facilitated instability waveform 280 and the display of the facilitated instability indices 282, polls the computer input devices for operator input, and relinquishes control back to the ASDP 128 and its simplex method to implement another AF parameter point as a pulse sequence.

FIG. 14 shows four buttons 286, 288, 290, and 292 that exemplify the sequence of operator inputs that control a diagnostic test embodied in the invention. After hooking a patient to the apparatus, the physician presses the "number of diagnostic trials" button 286 on the instability monitor 278 and enters the number of times the ASDP 128 shall initiate a search for a maximal instability index 276. For safety reasons, the ASDP 128 is permitted a limited number of searches, or diagnostic trials, without further physician intervention. The physician initiates a diagnostic test and a first diagnostic trial by pressing the "start/restart" button 288. Each time the "start/restart" button 288 is pressed by the physician, the physician initiates a new diagnostic test in the form of another search for instability by restarting the ASDP 128 and its simplex method with a newly constructed and unique starting simplex. In this way, a physician can manually reset the ASDP 128 to search again and again for a measure of a patient's myocardial electrical instability through the computation of another maximal instability index 276. The physician can stop the diagnostic test at any time by pressing the "stop" button 290. In this manner, a physician may operate the invention as many times as required to assess a patient's risk for SCD.

When the physician presses the "record and report results" button 292, the apparatus saves and prints a summary report of each diagnostic trial comprising an instability waveform 274 and index 276 determined by the trial to be a maximum instability data point. The physician may further request the display and output of a supporting, detailed analysis for each diagnostic trial. The apparatus keeps a record of each AF parameter point and its associated instability waveform 274 and index 276 that was evaluated by the simplex method during a search. The detailed analysis report comprises a structured listing of this intermediate search information, including the number of cardiac cycles involved, the number and location of each pulse, the amount of current for each pulse, the list of delivery and monitoring electrodes, the ECG signal frequency band of the ECG data analyzed, and the associated facilitated instability waveform 274 and index 276.

Description of the Hardware Elements

The hardware of the present invention implements any type of pulse sequences chosen by the simplex method of the ASDP, as will become apparent from the details of the hardware embodiments described below. The apparatus constructs, delivers, and monitors a plurality of current pulses to implement any AF parameter point chosen from a defined parameter-outcome search space. To implement an AF parameter point as an arbitrary but constrained pulse sequence, the invention embodies specific improvements over the prior art regarding the definition and shaping of a group of facilitating pulses.

The invention delivers a pulse at any point in time during a cardiac cycle. The invention delivers a pulse with any predetermined width and predetermined polarity. With the current delivery unit of the hardware implemented as a linear amplifier, the invention delivers a pulse with any predetermined shape or form. The invention delivers one or more pulses during a cardiac cycle. The invention delivers a plurality of uniquely determined pulses to a cardiac cycle without regard to the numbers, positions, or types of pulses delivered during any prior cardiac cycle. Therefore, the present instrument implements the delivery of a unique pulse pattern for each cardiac cycle and this pulse pattern can change across cardiac cycle boundaries during a pulse sequence.

The invention implements the pulse sequence delivered to a group of cardiac cycles from a plurality of output electrode pairs, called current injection ports. The apparatus delivers a pulse from a plurality of these ports, such that one or more electrodes act as an anode, and one or more electrodes act as a cathode. The simplex method's choice of a next AF parameter point defines the parameters that determine which one or more pairs of electrodes act as current injection ports for a pulse during the period of time the pulse is injected. The pairs of electrodes used to inject the current pulse can change from one pulse to the next. Each pulse in a pulse sequence can be delivered from current injection ports different from the current injection ports utilized for the delivery of prior pulses in a group of cardiac cycles. In this manner, the current is vectored across the heart in directions that are different from one pulse to the next.

Each cardiac cycle is monitored by acquiring ECG signals from a plurality of input electrodes, called voltage projection ports. Physically, the invention implements the hardware to permit an electrode to serve as a current injection port and a voltage projection port. The specific pulse parameters that characterize the delivery of a pulse in a pulse sequence changes the port type designation of an electrode over the time of a cardiac cycle.

The simplex method's choice of a AF parameter point also defines which one or more single electrodes serve as voltage projection ports before and after the delivery of a pulse. One or more of the electrodes specifically utilized as a current injection port for a pulse can be utilized as a voltage projection port before and after the delivery of the pulse. The individual electrodes utilized as voltage projection ports to monitor AF remain fixed during the period of time defined by the pulse sequence. Although these monitoring electrodes remain fixed during a pulse sequence, the simplex method's choice of a next AF parameter point can designate different electrodes as voltage projection ports for the next pulse sequence. Therefore, the present invention is as flexible implementing mutable spatial characteristics of a pulse sequence as it is implementing mutable temporal characteristics.

An AF parameter point and its associated pulse sequence vary the constituent pulses in time position, amplitude, polarity, and width. Therefore, a pulse sequence, as a group of distinct current pulses applied across a plurality of cardiac cycles, forms a portion of an arbitrary function or shape when the function or shape is viewed over a plurality of consecutive pulse sequences. The pulses in a plurality of pulse sequence, when viewed together, can form functions much like a sine wave, a sawtooth wave, or a square wave. This precision function shaping is a clear advantage of the preferred embodiments of this invention over the prior art.

To best understand the operation of the hardware elements, we describe the ten major hardware elements, or units, in detail. These ten hardware units are (1) a computer 104, utilized to operate the control program 116 and its ASDP 128 which (a) creates and sends pulse sequence instructions as commands to the hardware to implement AF and (b) monitors and analyzes digitized ECG signals for electrical instability, (2) a microcontroller unit 108, used to adaptively microcontrol all other hardware subsystems as directed by the control program 116 in the computer 104, and the eight hardware units that comprise the active facilitation (AF) unit 110: (3) digital to analog (D/A) and analog to digital (A/D) converters, (4) a current delivery unit, (5) a switching control circuitry, (6) ECG leads and electrodes, (7) amplifier protection circuitry and input buffers, (8) a right-leg driver circuitry, (9) a multiplexer, amplifier, and filtering (MAF) unit, and (10) a lead-failure detection unit.

The first hardware unit is a general purpose computer 104, such as a work station or high-performance personal computer (for example, a Pentium-based IBM PC or compatible machine). The computer 104 comprises standard components found in any general purpose computer, with a high-speed microprocessor connected through an addressing and data bus to its memory, floppy and hard disk drives, keyboard, monitor, and mouse. The computer 104 operates the control program 116 and ASDP 128 for the construction and control of the delivery of pulse sequences to a patient, the acquisition of a patient's ECG data which contain the measurable effects of pulse sequences on a patient's heart, and the analysis of the ECG data to determine the level of the patient's myocardial electrical instability and to determine a next pulse sequence. The control program 116 and ASDP 128 send pulse sequence instructions and data acquisition instructions to the microcontroller unit 108, which in turn implements these instructions by microcontrolling the other eight hardware subsystems 110.

Figure 15:
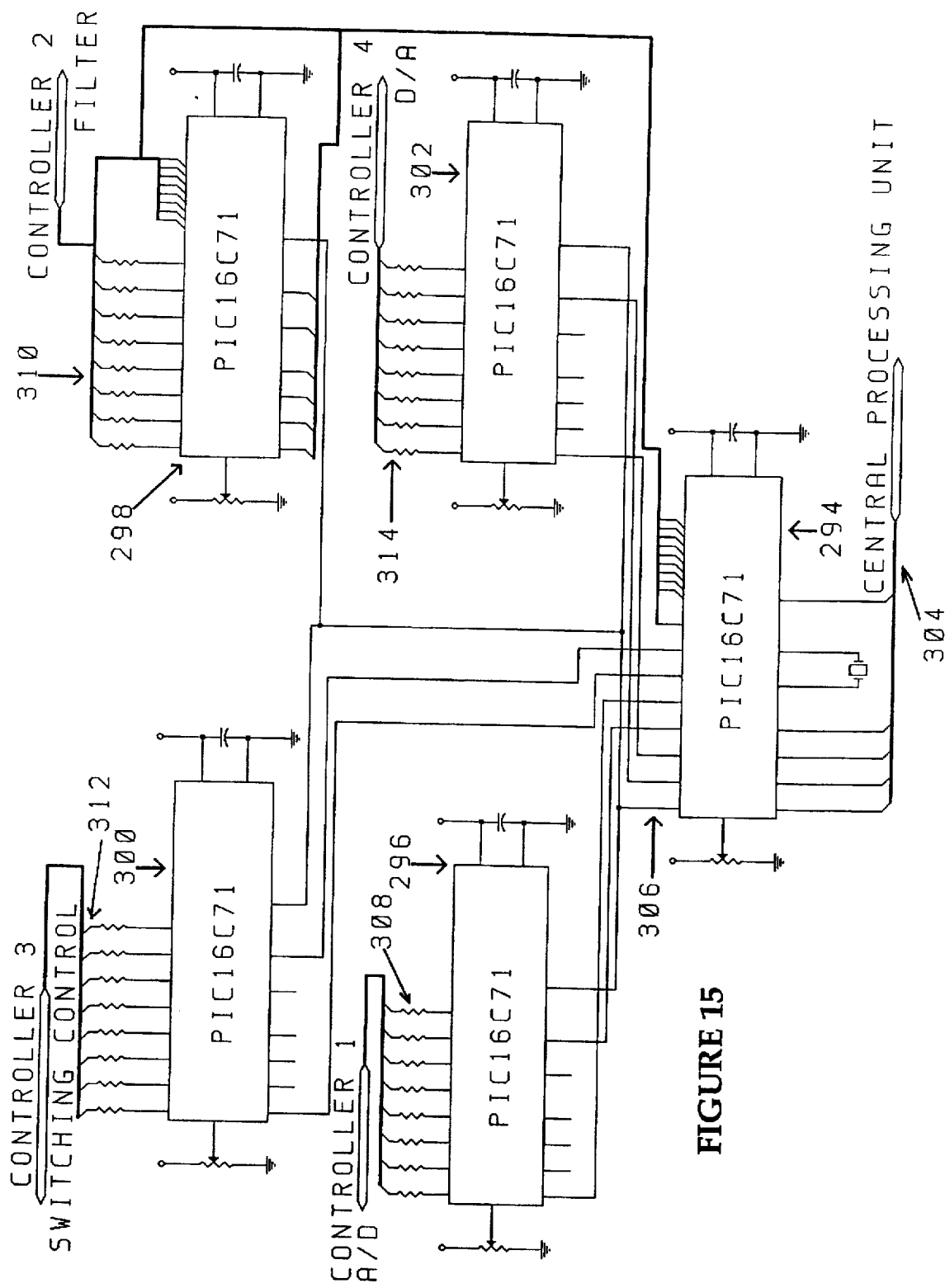
FIG. 15 is a schematic diagram of the hardware microcontroller chips that comprise the primary controller board which creates the connection and controlling means from the computer control program to the active facilitation unit.

Shown in FIG. 15, the second hardware unit, the microcontroller unit 108, is directed by the computer's ASDP 128 to adaptively microcontrol the other hardware units. The microcontroller unit 108 comprises five programmable integrated circuits 294, 296, 298, 300, and 302, each a PIC16C71, which is a high-performance, fully-static, 8-bit EPROM-based (erasable programmable read only memory) microcontroller, preferably manufactured by Microchip Technology Incorporated of Chandler, Ariz. A PIC16C71's high performance is due to single word instructions that are executed in one or two cycles, instruction pipe-lining, a large register set and separate instruction and data memory (Harvard architecture).

The microcontroller unit 108 is designed as a printed circuit board that contains the microcontroller chips 294, 296, 298, 300, and 302. The microcontroller unit 108 is connected to computer 104 by placing the circuit board inside computer 104 via a standard card slot. The microcontroller unit 108 is thereby connected to the computer addressing and data bus, and is thereby connected to the control program 116. The five PIC16C71 microcontrollers 294, 296, 298, 300, and 302 are divided into one master 294 and four slaves 296, 298, 300, and 302. Each microcontroller contains application specific machine code that implements its control logic and operation. The input 304 to the master microcontroller 294 is connected to the control program 116 through the computer bus interface and its output 306 is connected to the four slave microcontrollers 296, 298, 300, and 302. There is a single "master data clock" that goes from the master microcontroller 294 to all slaves. Each slave microcontroller has its own private data line(s) connected to the master microcontroller 294. Depending upon the type of instruction in an instruction packet, the master microcontroller 294 sends different data streams to one or more of the slave microcontrollers 296, 298, 300, and 302. The data streams are sent during the same clock cycles, thereby implementing a parallel processing of a pulse sequence.

The first slave microcontroller 296 synchronizes the timing 308 of a multiplexer, an amplifier and active filters and controls an A/D converter. The second slave microcontroller 298 controls the switching 310 of digital control words from a pre-constructed list of digital words in its EPROM, where each digital word represents a specific filter section implementation, into the circuitry of an active filter to alter the filtering characteristics of the active filter's low-pass and high-pass sections. The third slave microcontroller 300 connects to and controls 312 a bank of steady-state relay switches that are switched at appropriate times to deliver a current pulse through a designated pair of ECG electrodes during the same period of time that the remaining set of ECG electrodes are disconnected, or blanked. The fourth slave microcontroller 302 constructs and controls an output of digital words 314 to a D/A converter which represent the defining characteristics of pulse sequence parameters of each current pulse.

Figure 16:
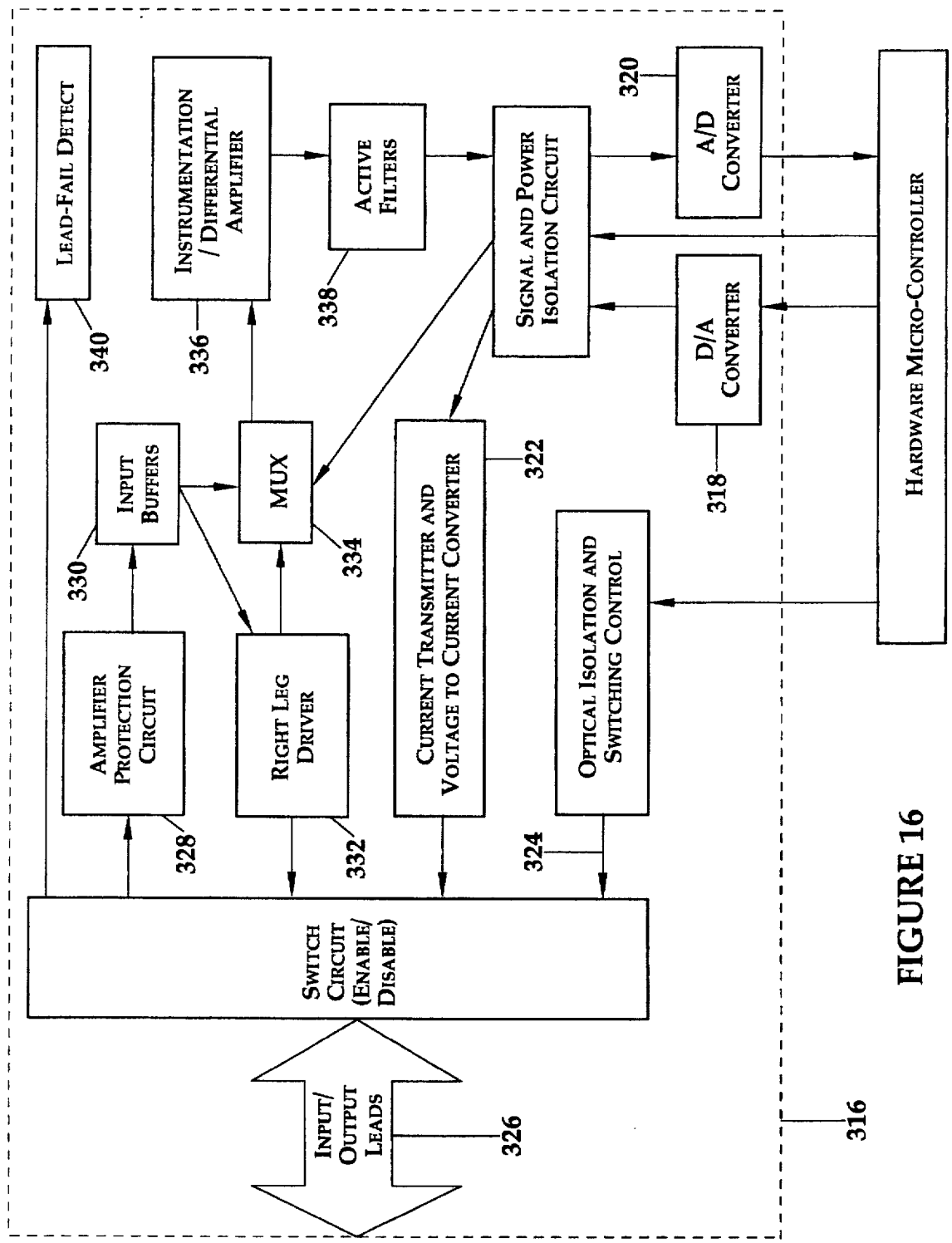
FIG. 16 is a block diagram of the hardware elements that implement the active facilitation unit, comprising the elements to the pulse delivery hardware and the elements to the ECG signal acquisition hardware.

FIG. 16 shows a block diagram of the eight units 318, 320, 322, 324, 326, 328, 330, 332, 334, 336, 338, and 340 that comprise the AF unit 110. These units, the third through tenth hardware units, are placed into a single, shielded enclosure 316.

Figure 17:
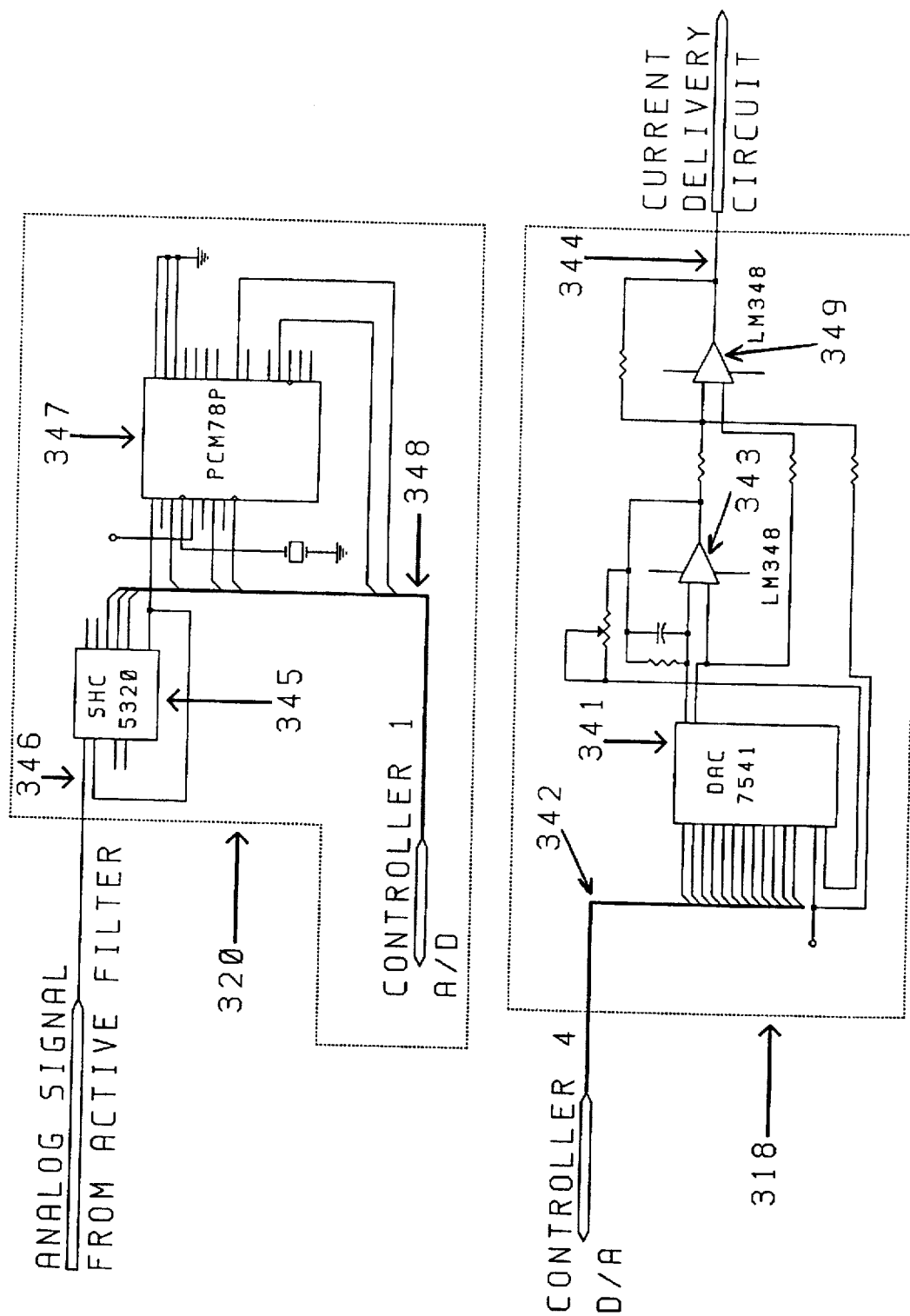
FIG. 17 is a schematic diagram of the digital to analog and the analog to digital conversion circuitry.

As shown in FIG. 16, the third hardware unit is the D/A converter 318 and A/D converter 320. Also shown in FIG. 17, the converters comprise a standard, high-performance, 12-bit D/A converter 318 and a standard, high-performance, 16-bit A/D converter 320.

The digital input pins 342 to the D/A converter 318 are connected to the fourth slave microcontroller 302, and the output analog channel 344 from the D/A converter 318 is connected to the precision current regulator 322 that serves as the current delivery system for the apparatus. The D/A converter comprises a D/A integrated circuit 341, an adjustable gain controller 343, and a unity gain buffer 349.

The serial input analog channel 346 to the A/D converter 320 is connected to the last section in the active filter circuit 338, and the serial digital output and control pins 348 are connected to the computer 104 via the timing and control of the first slave microcontroller 296. The A/D converter comprises a sample and hold integrated circuit 345 and a digitizing integrated circuit 347.

Figure 18:
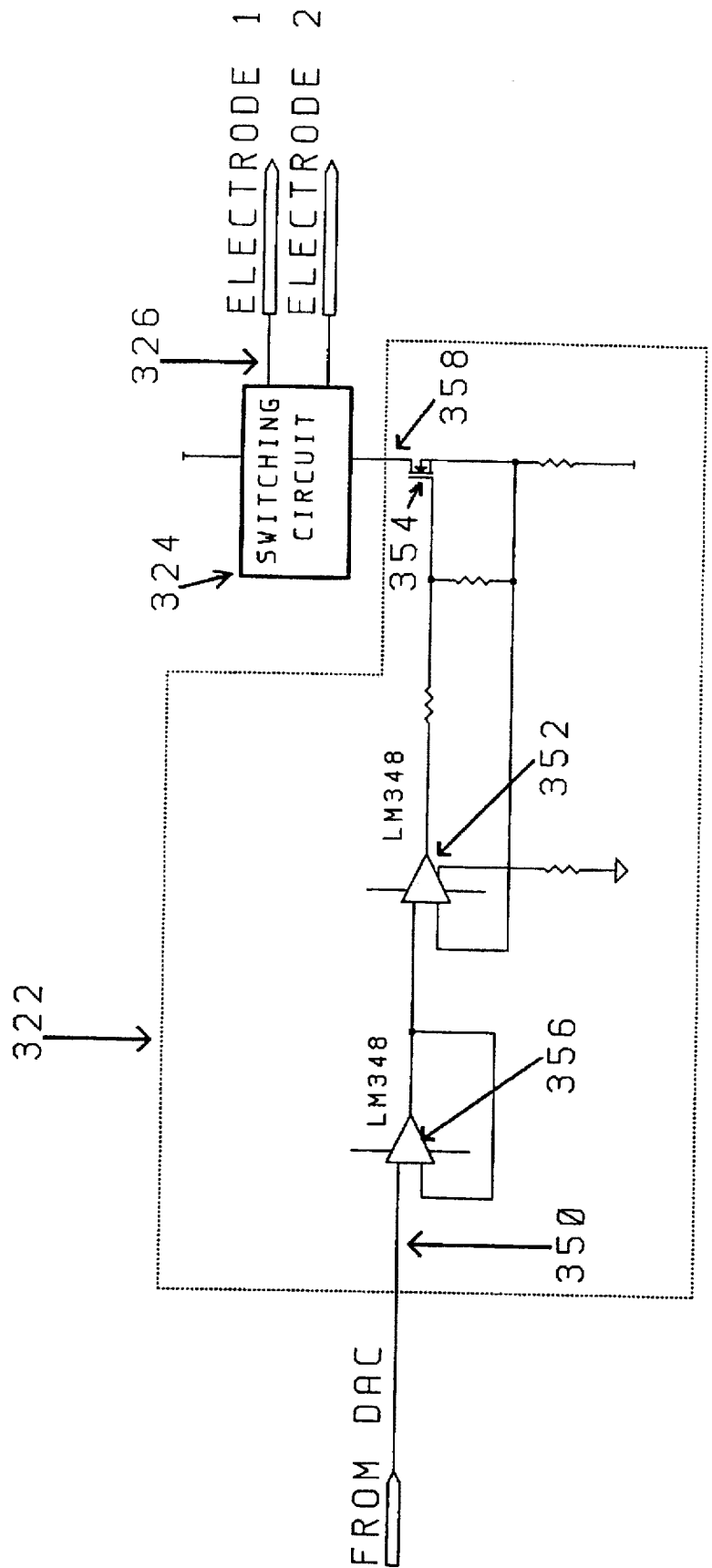
FIG. 18 is a schematic diagram of the current delivery system, comprised of two controlling operational amplifiers and a linearly operated power MOSFET, and the switching and connection means to the patient electrodes.

As shown in FIG. 16, the fourth hardware unit is the current delivery unit 322. Also shown in FIG. 18, the current delivery unit is a precision current regulator 322, modified from a standard circuit design as described in an application brief labeled AB-114 and published in Analog Device's 1983 Applications Reference Manual. The circuit allows variable input 350 ranging from −10V to +10V. The circuit regulates a stable and accurate current source that controls the current output over a range of 15V to 40V and from zero to 1A of current. The circuit comprises a unity gain buffer 356 and driver differential amplifier 352 that drives a power MOSFET device 354 to regulate and deliver a current pulse across a patient's electrodes 114. The power MOSFET 354 operates in the linear transfer region, making the output current 358 directly proportional to the voltage 350, thereby allowing the current delivery system 322 to regulate and deliver a pulse with its current 358 controlled by the input voltage 350 level and polarity, and further, with its pulsing shape exactly like that of the input voltage 350 waveform shape. More importantly, the precision current regulator 322 removes the possibly deleterious effects of varying impedance from one pulse to the next and from one patient to the next, since it precisely regulates a fixed amount of current 358 with respect to an input voltage value 350, regardless of the impedance. Therefore, the circuit 322 operates with a high open-loop gain to assure excellent current regulation. The input 350 to the current delivery unit 322 is connected to the output 344 of the D/A converter 318, and the output 358 from the current delivery unit 322 is connected to a patient's ECG electrodes 114 via a steady-state relay switching hardware unit 324. Therefore, parts of the second, third, and fourth hardware units 302, 318, 322, and 324 combine to provide a precisely regulated, programmable, digitally controlled, current source for injecting current pulses.

Figure 19:
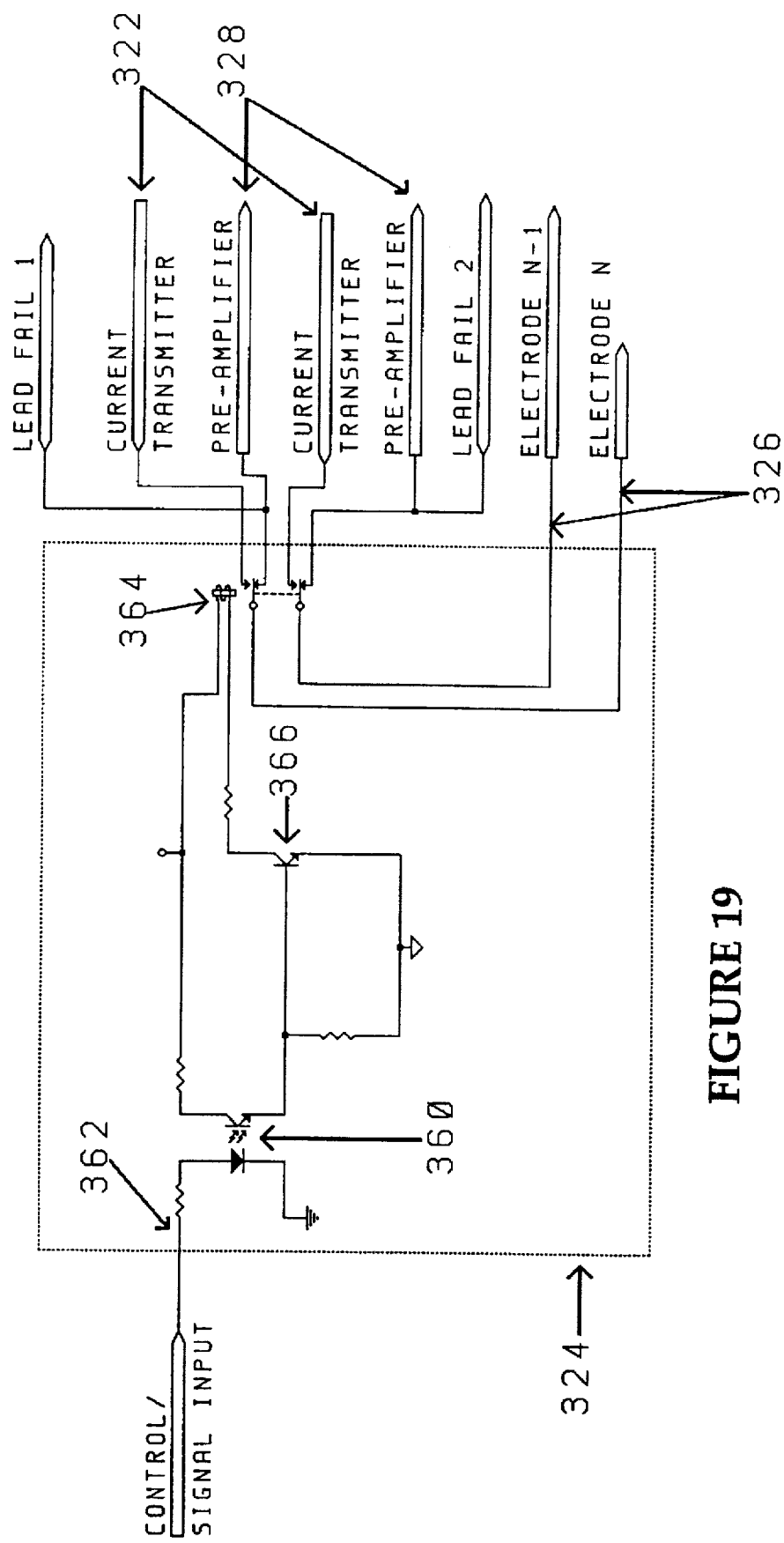
FIG. 19 is a schematic diagram of the optical isolation and switching control circuitry employing an extremely fast, steady-state relay.

As shown in FIG. 16, the fifth hardware unit is the switching control circuitry 324. Also shown in FIG. 19, the switching control circuitry 324 provides the apparatus with the ability to properly select electrodes 114 for pulse delivery and to properly select electrodes 114 for acquiring ECG signals. Each switching circuit 324 comprises an optical isolation circuit 360, which separates a power source 362 that drives the switching circuit from the circuit itself. A high-speed switching steady-state relay 364, or input/output module, connects the ECG electrodes 114 to the current delivery unit 322 and disconnects the ECG electrodes 114 from amplifier protection circuitry 328 during the delivery of a pulse. The steady-state relay 364, as implemented by a state-of-the-art input/output module, has an output range of 1 to 50 volts DC and 0.001 to 5 amperes, and is controlled by signals 362 sent from the third slave microcontroller 300, going through the optical isolation 360, and turning on the high-speed switching transistor 366. There is a switching control circuit 324 for each electrode pair that is utilized for the delivery of current pulses. As can be seen in FIG. 19, each electrode 114 in the pair can be utilized as a monitoring electrode 114.

The function of the steady-state relay 364 is two-fold. First, during the delivery of a current pulse (which occurs at a pre-determined point in time during a cardiac cycle), a bank of steady-state relays 364 connects a specified number of pairs of a patient's electrodes 114 to the current delivery unit 322 and temporarily disconnect the remaining number of ECG electrodes 114 from the apparatus, thereby implementing a "blanking" period during the time of the pulse delivery. Further, the bank of steady-state relays 364 must connect and disconnect various combinations of ECG electrodes 114 as quickly as possible, in order to provide the ASDP with as short a time for a current pulse as may be requested by the simplex method's searching strategy. Second, during periods of time in a cardiac cycle in which no delivery of a current pulse shall occur, the bank of steady-state relays 364 connects a plurality of patient's electrodes 114 to the ECG data acquisition units 328, 330, 332, 334, 336, 338, and 320 of the apparatus, and these electrodes 114 are arbitrary and change with each new pulse sequence. The connections allow the apparatus to collect ECG data to monitor and evaluate the effects of a current pulse on the electrical activity of the patient's heart. The switching unit 324 is connected to and controlled by the third slave microcontroller 300, as directed by the control program 116 and the master microcontroller 294. The third slave microcontroller 300 synchronizes the timing of the steady-state relays 364 to insure that the electrodes 114 that are not used for current delivery are disconnected from the apparatus before the pulse is delivered and that the same set of electrodes 114 can be reconnected immediately afterwards as required for monitoring.

Figure 20:
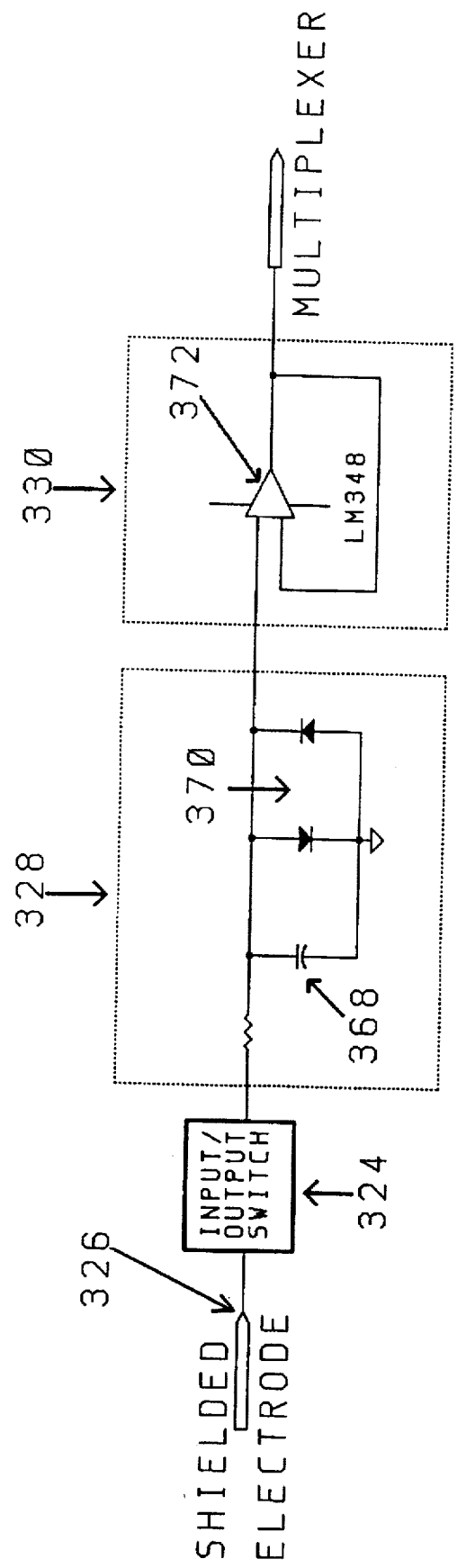
FIG. 20 is a schematic diagram of the patient electrode interface, showing the patient and signal protection circuitry and the ECG signal input buffers prior to the multiplexing hardware.

As shown in FIG. 16, the sixth hardware unit is the ECG leads 326 and electrodes 114. Also shown in FIG. 20, the ECG leads 326 and electrodes 114 provide an ability to deliver current pulses and to collect ECG signals. Special attention is given to the reduction of electrical and magnetic noise that can be induced on the leads 326 that are connected to a patient. Electromagnetic (EM) interference on the cabling can be created by high-frequency generators in the hospital, such as the electro-mechanical devices in the laboratory or operating room, the incandescent and neon lighting, or the operation of a near-by elevator. If the associated magnetic fields pass through ECG lead wires 326, a voltage is induced in the wiring. Reducing the effects of these magnetic fields will improve the circuit performance and the quality of the signals. Therefore, the invention enhances a conventional ECG system by completely shielding the ECG leads 326 in conjunction with an EM-shielding enclosure 316. Deleterious effects also occur as the fields go through the surface area between the wires 326 themselves. Therefore, these effects are minimized by creating a wiring harness by bundling the ECG lead wires 326 tightly together in a twisting pattern and leaving approximately 12 to 18 inches at the end of each ECG wire 326 to attach each wire 326 to an electrode 114 on a patient's body. The wiring harness is also kept close to a patient's body.

The unwanted EM field effects are further minimized by placing the third through tenth hardware units into the AF unit 110. The AF unit 110 is designed to be placed as close to a patient's body as possible, thereby significantly reducing the length of the ECG leads that are connected to a patient's body. Reducing the length of the wiring harness 326 that carries the ECG analog signals to the AF unit 110 to be digitized reduces the amount of wiring 326 that collects noise.

As shown in FIG. 16, the seventh hardware unit is the amplifier protection circuitry 328 and input buffers 330. Also shown in FIG. 20, the amplifier protection circuitry 328 and input buffers 330 connect the patient's ECG electrodes 114 to signal filtering and digitizing units via a multiplexer 334. The amplifier protection circuitry 328 provides an ability for the invention to protect itself against possible high voltages when the circuitry passes the ECG signals to the input buffers 330. The capacitor 368 and two diodes 370 shunt the inputs to ground. The capacitors 368 protect the input of an instrumentation amplifier 336 from the high voltages present during cardiac defibrillation, and provide patient protection in the event that high voltage should feed back through the instrumentation amplifier 336. In addition, the circuitry buffers the analog inputs. The op-amp 372 that comprises the buffering circuit 330 is configured as non-inverting, unity gain amplifier. The op-amp creates a very high input impedance that prevents the body electrode signals from being loaded down. There is an amplifier protection circuit 328 and an input buffer 330 for each electrode 114.

Figure 21:
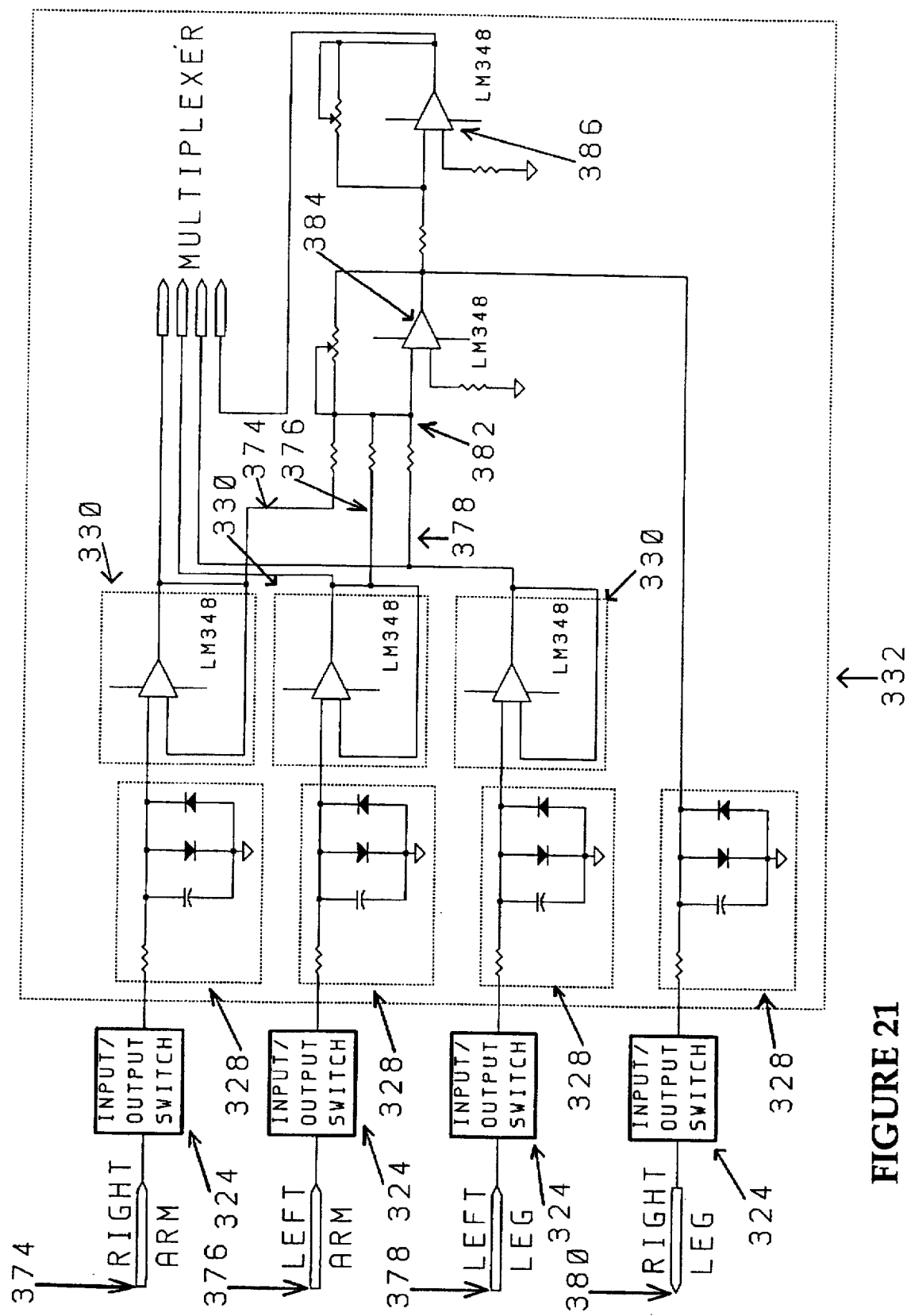
FIG. 21 is a schematic diagram of the right-leg driver used for the control and operation of the high-fidelity ECG signal hardware. The right-leg driver contains blanking switches and protection circuitry similar to the primary patient electrode interface.

As shown in FIG. 16, the eighth hardware unit is the right-leg driver circuitry 332. Also shown in FIG. 21, the right-leg driver circuitry 332 provides a reference point on a patient that is normally set to ground potential. The input to the right-leg driver 332 is received from three ECG limb leads, namely the right arm 374, left arm 376, and left leg 378. The output from the right-leg driver 332 is connected to an electrode 114 on the patient's right leg 380. The input of the three limb leads are summed 382 into an inverting op-amp 384 and fed back to the patient through the right leg lead 380. The composite signal from the three limb leads significantly reduces the common-mode noise in the system, since unwanted signals common to the three limb leads are fed back into a patient at 180 degrees out of phase with the original noise, thereby canceling the noise. The composite signal is again inverted in a second op-amp 386 and routed to the multiplexer 334 to form the reference signal against which all other input signals can be compared. The gain on the right-leg circuitry 332 is adjustable.

Figure 22:
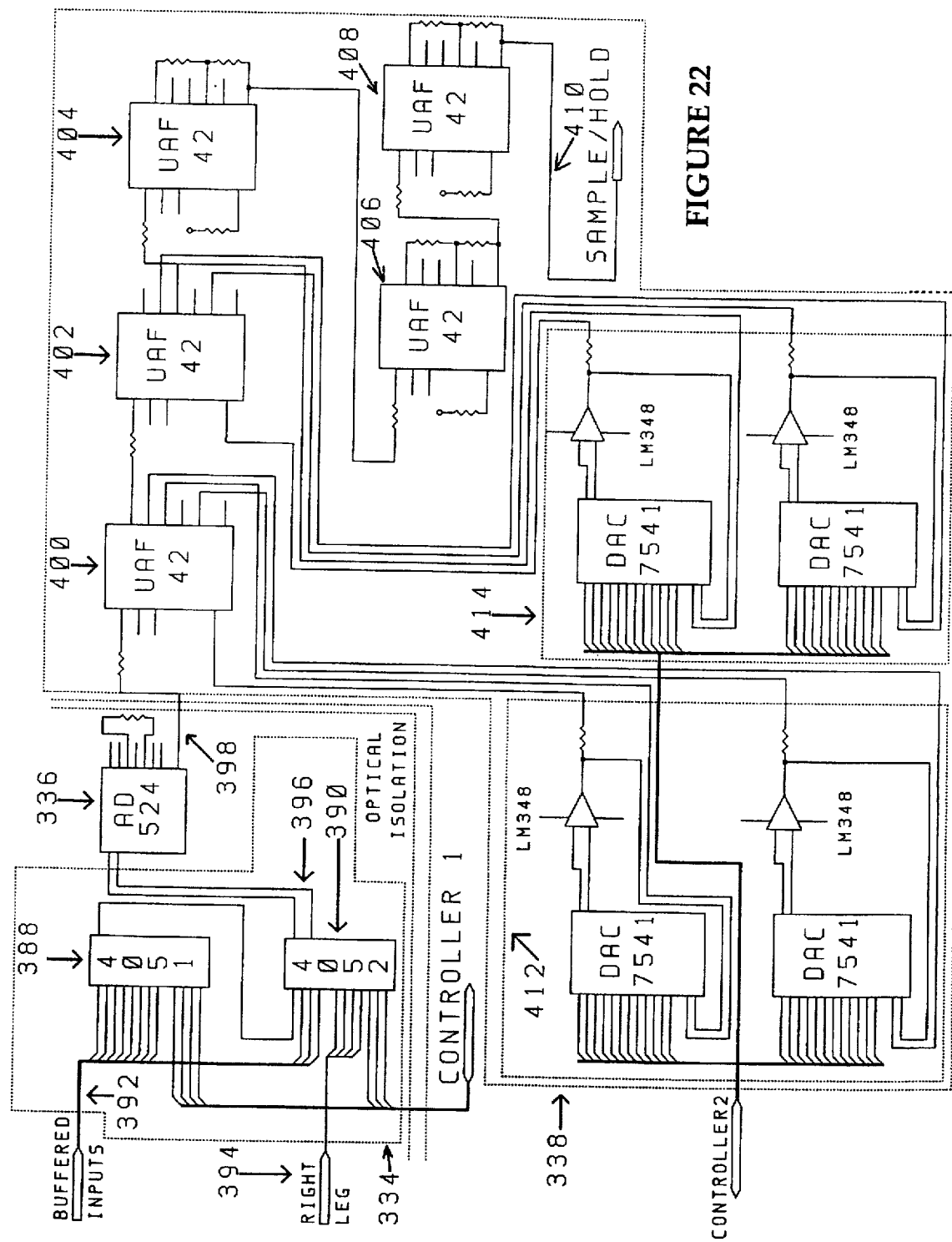
FIG. 22 is a schematic diagram of the multiplexer, amplifier, and filter circuitry for the selection and conditioning of a plurality of ECG signals, implementing an adaptive, active, analog filter comprising five, two-pole sections.

As shown in FIG. 16, the ninth hardware unit is the multiplexer 334, instrumentation amplifier 336, and filter elements 338. Also shown in FIG. 22, the multiplexer 334, amplifier 336, and filter 338 (MAF) unit provides an ability to select a plurality of ECG electrodes 114 for sampling and an ability to condition these electrodes 114 as input 346 to the A/D converter 320 by amplifying and filtering the associated ECG signals. The multiplexer 334 comprises two integrated circuits 388 and 390 and is controlled by the first slave microcontroller 296. The input to the multiplexer 334 are the ECG signals 392 and right leg driver signal 394 output by the signal buffers 330 in the amplifier protection and buffering unit. The multiplexer 334 serializes the analog inputs 392 and presets the serialized right-leg signal 394 synchronized to the other electrode inputs 392. The signals 396 from the multiplexer 334 are then fed into a precision differential amplifier 336, which amplifies the ECG signals 396 from 100 to 1000 times, depending on the value for a gain resistor. The amplifier's input is AC-coupled to keep DC voltages from saturating the differential amplifier, and rejects common-mode noise. The amplified ECG signals 398 are connected to an active filter 338 comprising a set of adaptable, active, analog filter sections 400, 402, 404, 406, and 408. The ECG signals 398 input to the active filter 338 are filtered to remove base-line wander, anti-alias, and extract pre-selected frequency bands. The ECG signals 410 are output from the filter 338 and to the A/D converter 320.

The MAF unit is controlled by the first slave microcontroller 296. The first slave microcontroller 296 and the MAF unit allow the ASDP 128, via instructions to the master microcontroller 294, to sample a plurality of ECG electrodes 114 at a total rate of up to 125,000 times a second, and can therefore sample as many as 25 different ECG electrodes 114 at 5000 times a second. The MAF unit samples ECG electrodes 114 at a rate sufficient for a proper time alignment 242 of extracted R-waves from a plurality of cardiac cycles. The MAF unit therefore comprises the elements of an ECG hardware that provide a superior, high-fidelity means to monitor ECG signals with the invention.

The apparatus utilizes an active filter 338 to separate the electrophysiologically meaningful ECG signals from the remainder of the signal, as well as to anti-alias the analog ECG signals when digitized. The principle element of active filter 338 is a universal, active, state-variable filter integrated circuit, preferably manufactured by Burr-Brown Corporation of Tucson, Ariz., and called an UAF42. The UAF42 is specifically designed for use in test equipment, medical instrumentation, and data acquisition systems, and is well suited for the apparatus to filter the ECG signals. Filters that are implemented with the analog, digitally programmable UAF42 are time-continuous and free from the switching noise and aliasing problems of similar programmable filters that use switched-capacitor topologies instead. The UAF42s 400, 402, 404, 406, and 408 of the active filter 338 provide two pole filter sections with low sensitivity of the filter parameters to external component values.

The low-pass section 400, high-pass section 402, and notch filter sections 404, 406, and 408 utilized by the invention are second-order sections of the Butterworth type, providing a complex-conjugate pair of poles for each section. As is well known, the natural frequency and Q of a pole pair determine the characteristic response of a filter section, and are determined by solving design equations for a predetermined filter configuration. In this way a plurality of 12-bit digital words can be predetermined and input to a D/A converter circuit 412 connected to a UAF42 to implement a plurality of low-pass sections 400 of the active filter 338. Similarly, a plurality of 12-bit digital words can be predetermined and input to a D/A converter circuit 414 connected to a UAF42 to implement a plurality of high-pass sections 402 of the active filter 338. At the time that the apparatus is turned on, the active filter 338 is implemented by cascading a 400 Hz low-pass section 400, a 0.25 Hz high-pass section 402, a 60 Hz notch 404, a 180 Hz notch 406 and a 300 Hz notch 408. The active filter 338 thereby eliminates base-line wander, inconsequential electrophysiological data, and high-frequency noise.

To dynamically restructure the filtering characteristics of the apparatus, a table of 12-bit digital words is constructed, such that each digital word in the table defines a predetermined low-pass section 400 or high-pass section 402. The filter word table and the logic instructions to adapt the filter sections 400 and 402 in real-time are implemented in the second slave microcontroller 298 of the microcontroller unit 108. Using the table of filter words, the second slave microcontroller 298 manipulates the low-pass section 400 and high-pass section 402 of the programmable active filter 338 to change, alter, adjust, or adapt the filtering band and filtering characteristics by presenting a corresponding digital word to each of the D/A converters 412 and 414 that control the analog inputs to the UAF42 chips 400 and 402.

The adaptive, programmable, active filter 338 provides the invention, and specifically the control program 116 and the ASDP 128, with the ability to automatically adjust a frequency range of the active filter 38 when designing and implementing a new step in the search for electrical anomalies in a patient's myocardium. As described above, an AF parameter point contains a parameter for the cut-off frequency for the low-pass filter section 400 and a parameter for the cut-off frequency for the high-pass filter section 402. Each parameter is a pointer into the table of filter words that define predetermined, low-pass sections 400 or high-pass sections 402. As is clear from the description of this preferred embodiment, the ability to dynamically adjust the filtering band at any time during a cardiac cycle is an important element of the teachings and operation of the invention.

The apparatus uses the active filter 338 to dynamically restructure the filtering characteristics applied to the ECG signals in a real-time manner. In a similar way, this filtering capability can be implemented by reconstructing software-based FIR filters in real-time, and dynamically implementing these FIR filters with programmable, DSP-based hardware designs. Although a DSP-based, band-adjustable filter is certainly constructable, such a hardware design does not lend itself to quick refinements in real-time, and can become overly complicated in its implementation. This limitation is overcome by using the UAF42-based active filter 338.

Figure 23:
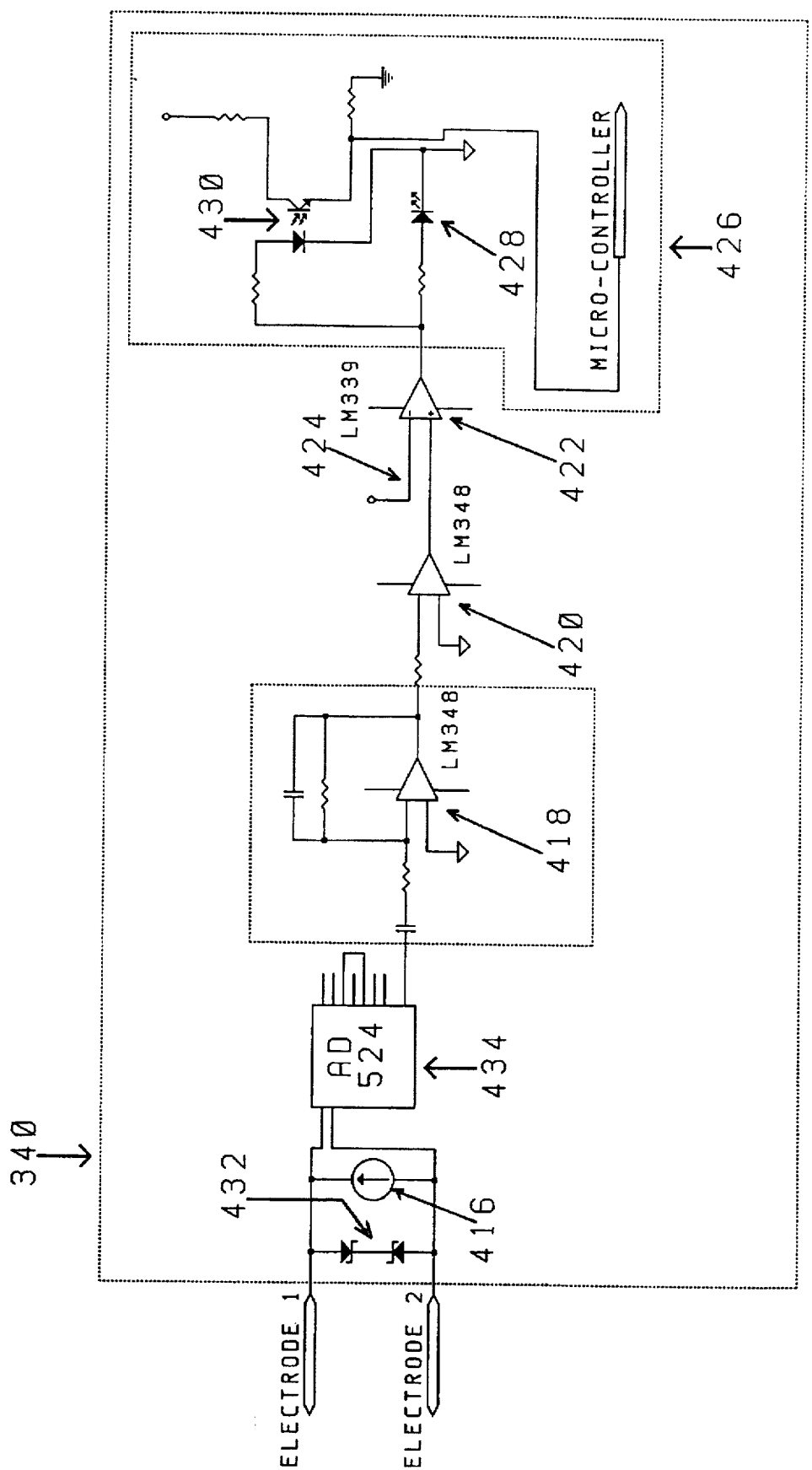
FIG. 23 is a schematic diagram of the lead-fail detection circuitry, which generates a very high frequency current continually through the patient's torso, detecting electrode failures with a threshold scheme.

As shown in FIG. 16, the tenth hardware unit is a lead-failure detection circuitry 340. Also shown in FIG. 23, the lead-failure detection circuitry 340 continually monitors for a failure in the invention's wires 326 or electrodes 114. The circuitry 340 produces a 40 kHz high-impedance current source 416, which is connected to designated pairs of electrodes 114. The current passes through a patient's body between the electrodes. The very high frequency signal 416 is separated from the much lower frequency ECG signals by filtering. As long as there is adequate electrode contact, the voltage drop across the body is relatively small. Initially poor electrode connections or electrode connections that worsen over a period of time can degrade signal quality, as can happen when an electrode's gel dries, an electrode disconnects from a patient's body, or a lead wire breaks from inappropriate or long-term handling. A poor electrode connection will therefore increase the impedance between itself and any other electrode considerably, and the voltage produced by the 40 kHz source 416 rises significantly. An instrumentation amplifier 434 and a bandpass filter 418 with a 40 kHz center frequency conditions and gains the voltage resulting from the current source, rectifies 420 the voltage signal, and passes the signal to a threshold detector 422. When the voltage exceeds a predetermined threshold 424, the threshold detector 422 sets off an alarm 426, comprising turning on a light emitting diode 428 or sending a digital signal 430 to the control program 116.

When an electrode 114 falls off a patient, the interelectrode impedance increases to infinity, resulting in the possibility of 40 kHz voltages high enough to cause damage to the apparatus. For this reason, a high-voltage protection circuit 432 is connected across the input terminals, implemented as back-to-back zener diodes 432. Peak amplitudes of the current can be hundreds of microamperes without any risk to a patient because the microshock hazard to the excitable tissue decreases exponentially as the frequency increases above 100 Hz.

The apparatus meets or exceeds the Association for the Advancement of Medical Instrumentation (AAMI) standards that establish safety and performance requirements for ECG devices, as described in the 1983 AAMI publication of their *American National Standard for Diagnostic Electrocardiographic Devices*. Specifically, the software and hardware elements for the invention sample a plurality of ECG signals simultaneously during a cardiac cycle. The software and hardware elements sample each ECG signal many thousands of times per second. The hardware sampling capability responds to time-varying signals well above and beyond the high-frequency response recommendations of the American Heart Association and AAMI as described in the standards publication mentioned above.

Description of Alternative Embodiments

As an alternative embodiment, the definition and implementation of the parameter-outcome space is expanded to include an adjustable number of cardiac cycles for each pulse sequence and an adjustable number of pulses per cycle. The ASDP and the simplex method select AF parameter points from an augmented search space that have pulse sequences of length from $N_1$ to $N_2$ cardiac cycles ($N_1 \leq N_2$), where the interval $[N_1, N_2]$ bounds the number of cardiac cycles. Similarly, the ASDP and the simplex method select AF parameter points from an augmented search space that have cycle pulse patterns of length from $P_1$ to $P_2$ pulses ($P_1 \leq P_2$), where the interval $[P_1, P_2]$ bounds the number of pulses.

As an alternative embodiment, the definition and implementation of the parameter-outcome space is expanded to include a description of a pulse's shape. Depending on the time scale of a pulse, the ASDP and the simplex method select AF parameter points from an augmented search space that define pulses to have triangular shapes, trapezoidal shapes, sine wave shapes, or other shapes that expand and extend the function of facilitating or inhibiting myocardial electrical activity so as to cause significant, subtle changes to occur from one cardiac cycle to the next. As described above, the invention's pulse delivery unit acts as a linear amplifier regarding the output of a pulse, so that the hardware implements any desired shaped for a current pulse.

Time alignment is a critical element in the evaluation of the ECG signals for electrical instability. Sampled systems exhibit a modulating effect caused by asynchronism between sampling rate and cardiac rate, sometimes called trigger jitter. This may be displayed as a difference in R-wave amplitudes from one cardiac cycle to the next, a phenomenon which is not physiologic but rather results from the sampling of different parts of an R-wave in each cardiac cycle. Time alignment minimizes the differences from one cardiac cycle to the next that are due to this sample and cardiac rate mismatch, thereby rendering such artificial differences to an insignificant level.

As an alternative embodiment, the invention, and specifically the AF procedure, operates a digital signal processor (DSP) board placed into the computer to detect and align each R-wave in the group of cardiac cycles associated with a pulse sequence. The purpose of this embodiment is to utilize more sophisticated procedures to extract and align the associated R-wave, thereby further reducing the effects of the sample-cardiac rate disparity while retaining the real-time ability to assess a group of cardiac cycles for the myocardial electrical instability facilitated by a pulse sequence.

As an alternative embodiment, the AF procedure waits until the ECG hardware has collected and stored a plurality of cardiac cycles for a pulse sequence into the computer memory before processing the cardiac cycles for myocardial electrical instability. The purpose of this embodiment is to utilize more sophisticated procedures to extract and align the associated R-waves without the need to implement these methods with DSP-based software and hardware elements.

As an alternative embodiment, the AF procedure extracts and time aligns the cardiac cycle based on one or more morphological features in the region of the T-wave, thereby significantly reducing the substantial alignment jitter that is seen from one T-wave to another when cardiac cycles are aligned using a region of the R-wave. The AF procedure constructs a facilitated instability waveform and index for a pulse sequence based on the myocardial electrical activity manifested in the T-wave. The T-wave is well-known to be generated by the repolarization of the ventricles, corresponding to the end of phase 2 and phase 3 of the cardiac action potential. The duration of the T-wave is considerably longer than that of the R-wave because repolarization does not spread as a rapidly propagated wave front. The T-wave is determined largely by local factors that influence the outward cell currents that end the action potentials in the various regions of the heart. The purpose of this alternative embodiment is to utilize the T-wave portion of the ECG signals, which contains independent diagnostic electrical information compared to that of the R-wave. Therefore, AF analysis of the T-wave provides a facilitated instability waveform and index orthogonal to that calculated for the R-wave.

As an additional feature of this alternative embodiment, extracting and time aligning the R-wave for a cardiac cycle is performed jointly with a similar process for the T-wave. The apparatus computes an RT instability waveform pair and an RT index pair from the sets of R-waves and T-waves of a pulse sequence. Many different combinations of the RT waveform pair or RT index pair can be considered for further analysis, display, or reporting, such as a weighted summation, difference, average, or supremum.

As an alternative embodiment, the AF procedure utilizes the diagnostic information stored during a diagnostic trial to construct a "global-temporal" instability waveform or index across a plurality of pulse sequences. The AF procedure combines the instability waveforms or indices associated with a plurality of pulse sequences for a predetermined ECG signal by combining means, including a weighted average, median, minimum, or maximum.

As an alternative embodiment, the AF procedure utilizes the diagnostic information stored during a diagnostic trial to construct a "global-spatial" instability waveform or index across a plurality of predetermined monitored ECG signals. The AF procedure combines the instability waveforms or indices associated with the ECG signals by combining means, including a weighted average, median, minimum, or maximum.

ECG signals are influenced by a variety of factors. These factors include the size, location, and orientation of a patient's heart relative to an electrode's position, and affect the magnitude of an ECG signal. Other physiological activities and functions of the patient, such as talking, breathing, and moving the body affect the magnitude of an ECG signal as well. Most of these activities are eliminated by having a patient lie quietly in a supine position during a period of time that a physician diagnoses the patient with the apparatus.

A diagnostic test typically requires several minutes of time. This period of time is normally more time than a patient can comfortably hold his or her breath. Some patients may even be unconscious, and so cannot hold their breath during the testing period. For these reasons, it is not desirable to eliminate breathing during a period of ECG monitoring or analysis. Breathing causes variability in the ECG signal due primarily to the changes in the geometry of the chest and tilting of the heart during lung and pulmonary function. The problem due to breathing is accentuated further when a method of assessing myocardial electrical instability is a measure of electrical variability from one cardiac cycle to the next.

As an alternative embodiment, the ASDP computes the level of a patient's myocardial electrical instability utilizing a null pulse sequence of a predetermined length. The ASDP initiates the AF procedure with the null pulse sequence. The AF procedure applies the null sequence, constructing a natural instability waveform and index from the associated monitored cardiac cycles, and supplies the waveform and index to the ASDP. The resulting instability waveform and index ($I_{AF,N}$) establish a baseline measurement of a patient's myocardial electrical instability, which we call the patient's natural electrical instability. The natural instability waveform or index is used to correct or normalize a facilitated instability waveform or index for the effects of breathing on the ECG signals. As a first method, the AF procedure subtracts the natural instability waveform from each facilitated instability waveform before calculating an instability index, thereby removing the amount of electrical instability typical of a patient without facilitation. As a second method, the AF procedure subtracts the natural instability index from each facilitated instability index, thereby removing the amount of electrical instability typical of a patient without facilitation. A breathing-corrected index for facilitated myocardial electrical instability is $$I_{AF,BC} = \max(0, I_{AF} - I_{AF,N}).$$

As a third method, the AF procedure divides or normalizes each facilitated instability index by the natural instability index, thereby calculating a ratio of facilitated to natural instability. The instability ratio is displayed and reported as a breathing-corrected index for facilitated myocardial electrical instability, namely $$I_{AF,BC} = \max(1, I_{AF}/I_{AF,N}).$$

A patient's heart can be facilitated and a patient's cardiac cycle can be recorded both by electric and magnetic techniques. The electric techniques have been discussed in detail in these preferred embodiments. The adaptation of these methods and apparatus to magnetic techniques will be obvious to those skilled in the art.

Those skilled in the art will recognize that the embodiments disclosed herein are exemplary in nature and that various changes can be made therein without departing from the scope and the spirit of this invention. In that regard, as many changes as are possible to the embodiments of this invention utilizing the teachings thereof, the descriptions above, and the accompanying drawings should be interpreted in the illustrative and not the limited sense.

That which is claimed is:

1. An improved electrocardiography apparatus of the type having a plurality of electrocardiographic leads adapted to be connected to a patient's body, wherein the improvement comprises:
   (a) a computer;
   (b) an active facilitation unit connected to said electrocardiographic leads;
   (c) a controller unit connected to said computer and connected to said active facilitation unit; and
   (d) a control program operating in said computer and connected to said active facilitation unit via said controller unit, and comprising:
      (i) an adaptive search and discover procedure connected to said active facilitation unit; and
      (ii) an operator interface and search override procedure connected to said adaptive search and discover procedure, whereby said patient is accessed for myocardial electrical instability.

2. The apparatus of claim 1, wherein said computer is selected from the group consisting of a work station and a high-performance personal computer.

3. The apparatus of claim 1, wherein said active facilitation unit comprises:
   (a) a current delivery unit;
   (b) a switching control means connected to said current delivery unit and connected to said electrocardiographic leads, whereby said switching control means are simultaneously utilized to deliver current to said electrocardiographic leads and to monitor a plurality of electrocardiographic signals derived from said electrocardiographic leads; and
   (c) a sampling filter means connected to said switching control means and connected to said controller unit, whereby said monitored electrocardiographic signals are filtered, sampled, and recorded into said computer via said controller unit.

4. The apparatus of claim 3, wherein said current delivery unit comprises:

(a) a precisely regulated current source; and (b) a digital to analog converter connected to said precisely regulated current source and connected to said controller unit, whereby said current delivery unit is programmable, based on input voltage, and without regard to patient impedance levels.

5. The apparatus of claim 3, wherein said switching control means comprises:

(a) a plurality of high-speed switching steady-state relays connected to said current delivery unit and connected to said electrocardiographic leads; and (b) a plurality of high-speed switching transistors connected to said high-speed switching steady-state relays and connected to said controller unit, whereby said switching control means is programmable and precisely timed.

6. The apparatus of claim 3, wherein said sampling filter means comprises:

(a) a multiplexer connected to said switching control means;

(b) a state-variable active filter connected to said multiplexer; and (c) an analog to digital converter connected to said state-variable active filter and connected to said controller unit.

7. The apparatus of claim 6, wherein said state-variable active filter comprises:

(a) a plurality of state-variable analog low-pass filters connected to said multiplexer;

(b) a plurality of digital to analog converters connected to said low-pass filters and connected to said controller unit;

(c) a plurality of state-variable analog high-pass filters connected to said low-pass filters and connected to said analog to digital converter; and (d) a plurality of digital to analog converters connected to said high-pass filters and connected to said controller unit, whereby said state-variable active filter is programmable and precisely timed.

8. The apparatus of claim 1, wherein said controller unit comprises a plurality of programmable microcontrollers integrated on a printed circuit card and connected to said computer via a standard card slot.

9. The apparatus of claim 8, wherein said plurality of programmable microcontrollers comprises a master microcontroller and a plurality of slave microcontrollers individually connected to said master microcontroller.

10. The apparatus of claim 1, wherein said adaptive search and discover procedure comprises:

(a) an adaptive search procedure connected to said active facilitation unit, said adaptive search procedure being utilized to inject a plurality of current pulses into said patient's body via said active facilitation unit and to monitor a plurality of electrocardiographic signals via said active facilitation unit; and (b) a discover procedure connected to said adaptive search procedure and connected to said active facilitation unit, said discover procedure being utilized to detect facilitated changes in said electrocardiographic signals caused by said current injection, whereby said adaptive search and discover procedure maximizes said facilitated changes.

11. The apparatus of claim 10, wherein said adaptive search procedure comprises:

(a) a plurality of pulse sequence descriptors resident in said control program;

(b) an optimization procedure operating in said computer, connected to said pulse sequence descriptors, and connected to said discover procedure; and (c) a control procedure connected to said optimization procedure and connected to said active facilitation unit, and comprising:

(i) means for transforming said pulse sequence descriptors into current injection instructions and electrocardiographic lead monitoring instructions; and (ii) means for transmitting said injection instructions and said monitoring instructions via said controller unit to said active facilitation unit, said control procedure being utilized to inject a plurality of current pulses into said patient's body, whereby said adaptive search procedure maximizes said facilitated changes.

12. The apparatus of claim 10, wherein said discover procedure comprises:

(a) means for collecting facilitated electrocardiographic signal changes into a facilitated instability waveform and connected to said active facilitation unit; and (b) means for summing said facilitated instability waveform connected to said collecting means and connected to said adaptive search procedure, said summing means being utilized to compute a facilitated instability index, whereby said adaptive search and discover procedure maximizes said facilitated instability index.

13. An improved electrocardiography apparatus of the type having a plurality of electrocardiographic leads adapted to be connected to a patient's body, wherein the improvement comprises:

(a) an active facilitation unit connected to said electrocardiographic leads and comprising:

(i) a current delivery unit connected to said electrocardiographic leads; and (ii) a sampling filter means connected to said electrocardiographic leads;

(b) a controller unit connected to said active facilitation unit;

(c) a computer connected to said controller unit;

(d) an adaptive search procedure operating in said computer and connected to said controller unit, said adaptive search procedure being utilized to inject a plurality of current pulses into said patient's body via said current delivery unit and to monitor a plurality of electrocardiographic signals via said sampling filter means;

(e) a discover procedure operating in said computer, connected to said adaptive search procedure, and connected to said controller unit, said discover procedure being utilized to detect facilitated changes in said electrocardiographic signals caused by said current injection; and (f) an operator interface and search override procedure operating in said computer and connected to said adaptive search procedure, whereby said adaptive search procedure maximizes said facilitated changes, whereby said patient is assessed for myocardial electrical instability.

14. An improved electrocardiography apparatus of the type having a plurality of electrocardiographic leads adapted to be connected to a patient's body, wherein the improvement comprises:
- (a) an active facilitation unit connected to said electrocardiographic leads and comprising:
  - (i) a precisely regulated current source connected to said electrocardiographic leads;
  - (ii) a multiplexer connected to said electrocardiographic leads; and
  - (iii) a state-variable active filter connected to said multiplexer;
- (b) a plurality of programmable microcontrollers connected to said active facilitation unit;
- (c) a computer, having a control program connected to said programmable microcontrollers;
- (d) a plurality of pulse sequence descriptors resident in said control program;
- (e) an optimization procedure operating in said computer and connected to said pulse sequence descriptors;
- (f) a control procedure connected to said optimization procedure and connected to said programmable microcontrollers, and comprising:
  - (i) means for transforming said pulse sequence descriptors into current injection instructions and electrocardiographic lead monitoring instructions; and
  - (ii) means for transmitting said injection instructions and said monitoring instructions via said programmable microcontrollers to said active facilitation unit, said control procedure being utilized to inject a plurality of current pulses into said patient's body and to record a plurality of electrocardiographic signals from said electrocardiographic leads;
- (g) means for collecting facilitated changes in said recorded electrocardiographic signals caused by said current injection into a facilitated instability waveform and connected to said computer;
- (h) means for summing said facilitated instability waveform into a facilitated instability index, connected to said collecting means, and connected to said optimization procedure, whereby said optimization procedure maximizes said facilitated instability index; and
- (i) an operator interface and search override procedure operating in said computer and connected to said optimization procedure, whereby said patient is assessed for myocardial electrical instability.

15. An improved electrocardiography apparatus of the type having a plurality of electrocardiographic leads adapted to be connected to a patient's body, wherein the improvement comprises:
- (a) a computer, having a control program;
- (b) a controller unit connected to said computer and connected to said electrocardiographic leads, said controller unit utilized to monitor said electrocardiographic leads and to record a plurality of electrocardiographic signals into said computer from said electrocardiographic leads;
- (c) means for detecting natural changes in said recorded electrocardiographic signals and operating in said computer; and
- (d) means for automatically adapting said lead monitoring operating in said computer, connected to said means for detecting said natural changes, and connected to said controller unit, said means for automatically adapting said lead monitoring being utilized to maximize said natural changes, whereby said patient is assessed for myocardial electrical instability.

16. The apparatus of claim 15, wherein said controller unit comprises:
- (a) a switching control means connected to said computer and connected to said electrocardiographic leads, said switching control means being utilized to monitor a plurality of electrocardiographic signals from said electrocardiographic leads; and
- (b) a sampling filter means connected to said switching control means and connected to said computer, said sampling filter means being utilized to filter, sample, and record said electrocardiographic signals into said computer.

17. The apparatus of claim 16, wherein said controller unit further comprises a plurality of programmable microcontrollers connected to said computer and connected to said switching control means, whereby said switching control means is programmable and precisely timed.

18. The apparatus of claim 16, wherein said controller unit further comprises a plurality of programmable microcontrollers connected to said computer and connected to said sampling filter means, whereby said sampling filter means is programmable and precisely timed.

19. The apparatus of claim 16, wherein said switching control means comprises:
- (a) a plurality of high-speed switching steady-state relays connected to said electrocardiographic leads; and
- (b) a plurality of high-speed switching transistors connected to said high-speed switching steady-state relays and connected to said computer, whereby said switching control means is programmable and precisely timed.

20. The apparatus of claim 16, wherein said sampling filter means comprises:
- (a) a multiplexer connected to said switching control means;
- (b) a state-variable active filter connected to said multiplexer; and
- (c) an analog to digital converter connected to said state-variable active filter and connected to said computer.

21. The apparatus of claim 20, wherein said state-variable active filter comprises:
- (a) a plurality of state-variable analog low-pass filters connected to said multiplexer;
- (b) a plurality of digital to analog converters connected to said low-pass filters and connected to said computer;
- (c) a plurality of state-variable analog high-pass filters connected to said low-pass filters and connected to said analog to digital converter; and
- (d) a plurality of digital to analog converters connected to said high-pass filters and connected to said computer, whereby said state-variable active filter is programmable and precisely timed.

22. The apparatus of claim 15, wherein said means for detecting natural changes comprises:
- (a) means for collecting natural changes in said recorded electrocardiographic signals into a natural instability waveform and connected to said computer; and
- (b) means for summing said natural instability waveform connected to said collecting means and connected to said means for automatically adapting said lead monitoring, said summing means being utilized to compute a natural instability index,
whereby said means for automatically adapting said lead monitoring maximizes said natural instability index.

23. The apparatus of claim 15, wherein said means for automatically adapting said lead monitoring comprises:
   (a) a plurality of pulse sequence descriptors resident in said control program;
   (b) an optimization procedure operating in said computer, connected to said pulse sequence descriptors, and connected to said means for detecting said natural changes; and
   (c) a control procedure connected to said optimization procedure and connected to said controller unit, and comprising:
      (i) means for transforming said pulse sequence descriptors into electrocardiographic lead monitoring instructions; and
      (ii) means for transmitting said monitoring instructions to said controller unit,
whereby said optimization procedure maximizes said natural changes.

24. The apparatus of claim 15, wherein said improvement further comprises:
   (a) an active facilitation unit connected to said controller unit and connected to said electrocardiographic leads, said active facilitation unit being utilized to inject a plurality of electromagnetic energy pulses into said patient's body via said electrocardiographic leads;
   (b) means for detecting facilitated changes in said recorded electrocardiographic signals caused by said energy injection and connected to said computer; and
   (c) means for automatically adapting said energy injection to maximize said detection of said facilitated changes and connected to said means to detect said facilitated changes.

25. The apparatus of claim 24, wherein said active facilitation unit comprises:
   (a) a current delivery unit; and
   (b) a switching control means connected to said current delivery unit and connected to said controller unit, whereby said switching control means are simultaneously utilized to deliver current to said electrocardiographic leads and to monitor said electrocardiographic leads.

26. The apparatus of claim 24, wherein said means for detecting facilitated changes comprises:
   (a) means for collecting facilitated changes in said recorded electrocardiographic signals into a facilitated instability waveform and connected to said computer; and
   (b) means for summing said facilitated instability waveform connected to said collecting means and connected to said means for automatically adapting said energy injection, said summing means being utilized to compute a facilitated instability index,
whereby said means for automatically adapting said energy injection maximizes said facilitated instability index.

27. The apparatus of claim 24, wherein said means for automatically adapting said energy injection comprises:
   (a) a plurality of pulse sequence descriptors resident in said control program;
   (b) an optimization procedure operating in said computer, connected to said pulse sequence descriptors, and connected to said means for detecting said facilitated changes; and
   (c) a control procedure connected to said optimization procedure and connected to said active facilitation unit, and comprising:
      (i) means for transforming said pulse sequence descriptors into current injection instructions; and
      (ii) means for transmitting said injection instructions via said controller unit to said active facilitation unit,
whereby said optimization procedure maximizes said facilitated changes.

28. The apparatus of claim 24, wherein said improvement further comprises means to remove said natural changes from said facilitated changes connected to said means for detecting said natural changes and connected to said means for detecting said facilitated changes, whereby said myocardial electrical instability is assessed and confounding effects of naturally occurring physiological variations are removed from said assessment of myocardial electrical instability.

29. An improved electrocardiography apparatus of the type having a plurality of electrocardiographic leads adapted to be connected to a patient's body, wherein the improvement comprises:
   (a) a computer, having a control program;
   (b) a switching control means connected to said computer and connected to said electrocardiographic leads, said switching control means being utilized to monitor a plurality of electrocardiographic signals from said electrocardiographic leads;
   (c) a sampling filter means connected to said switching control means and connected to said computer, said sampling filter means being utilized to filter, sample, and record said electrocardiographic signals into said computer;
   (d) means for detecting natural changes in said recorded electrocardiographic signals and operating in said computer;
   (e) a plurality of pulse sequence descriptors resident in said control program;
   (f) an optimization procedure operating in said computer, connected to said pulse sequence descriptors, and connected to said means for detecting said natural changes; and
   (g) a control procedure connected to said optimization procedure and connected to said switching control means, and comprising:
      (i) means for transforming said pulse sequence descriptors into electrocardiographic lead monitoring instructions; and
      (ii) means for transmitting said monitoring instructions to said switching control means, whereby said optimization procedure maximizes said natural changes,
whereby said patient is assessed for myocardial electrical instability.

30. An improved electrocardiography apparatus of the type having a plurality of electrocardiographic leads adapted to be connected to a patient's body, wherein the improvement comprises:
   (a) a computer, having a control program;
   (b) a switching control means connected to said computer and connected to said electrocardiographic leads, said switching control means being utilized to monitor a plurality of electrocardiographic signals from said electrocardiographic leads; and
   (c) a sampling filter means connected to said switching control means and connected to said computer, said sampling filter means being utilized to filter, sample, and record said electrocardiographic signals into said computer;

(d) means for detecting natural changes in said recorded electrocardiographic signals and operating in said computer; and (e) an active facilitation unit connected to said switching control means, said active facilitation unit being utilized to inject a plurality of electromagnetic energy pulses into said patient's body via said electrocardiographic leads;

(f) means for detecting facilitated changes in said recorded electrocardiographic signals caused by said energy injection and operating in said computer; and (g) a plurality of pulse sequence descriptors resident in said control program;

(h) an optimization procedure operating in said computer, connected to said pulse sequence descriptors, connected to said means for detecting said natural changes, and connected to said means for detecting said facilitated changes;

(i) a control procedure connected to said optimization procedure, connected to said switching control means, and connected to said active facilitation unit, comprising:

(i) means for transforming said pulse sequence descriptors into electrocardiographic lead monitoring instructions and current injection instructions; and (ii) means for transmitting said monitoring instructions via said switching control means to said sampling filter means, whereby said optimization procedure maximizes said natural changes;

(iii) means for transmitting said injection instructions via said switching control means to said active facilitation unit, whereby said optimization procedure maximizes said facilitated changes;

(j) means for removing said natural changes from said facilitated changes connected to said means for detecting said natural changes and connected to said means for detecting said facilitated changes, whereby said myocardial electrical instability is assessed and confounding effects of naturally occurring physiological variations are removed from said assessment of myocardial electrical instability.

* * * * *